(12) United States Patent
Balandrin et al.

(10) Patent No.: US 6,617,358 B1
(45) Date of Patent: Sep. 9, 2003

(54) ANTICONVULSANT AND CENTRAL NERVOUS SYSTEM-DEPRESSING BIS (FLUOROPHENYL)ALKYLAMIDES AND THEIR USES

(75) Inventors: Manuel F. Balandrin, Sandy, UT (US); Bradford C. VanWagenen, Salt Lake City, UT (US); Linda D. Artman, Salt Lake City, UT (US); Alan L. Mueller, Salt Lake City, UT (US); Daryl Smith, Salt Lake City, UT (US); Scott T. Moe, Salt Lake City, UT (US)

(73) Assignee: NPS Pharmaceuticals, Inc., Salt Lake City, UT (US)

(*) Notice: Subject to any disclaimer, the term of this patent is extended or adjusted under 35 U.S.C. 154(b) by 0 days.

(21) Appl. No.: 09/587,179

(22) Filed: Jun. 2, 2000

Related U.S. Application Data

(63) Continuation of application No. PCT/US98/26315, filed on Dec. 9, 1998.
(60) Provisional application No. 60/069,005, filed on Dec. 10, 1997.

(51) Int. Cl.$^7$ .............................................. A61K 31/165

(52) U.S. Cl. ..................... 514/617; 514/557; 514/568

(58) Field of Search .................... 564/181; 514/617, 514/557, 568

(56) References Cited

U.S. PATENT DOCUMENTS

| | | | | |
|---|---|---|---|---|
| 3,120,434 A | * | 2/1964 | Pohland et al. | ............... 71/2.6 |
| 4,603,145 A | * | 7/1986 | DeVries et al. | ............. 514/539 |
| 5,506,268 A | | 4/1996 | Balandrin et al. | ........... 514/629 |

FOREIGN PATENT DOCUMENTS

| | | |
|---|---|---|
| WO | 95/21612 | 8/1995 |
| WO | 96/05818 | 2/1996 |

OTHER PUBLICATIONS

Sindler et al, Coll. Czech. Chem. Commun., vol. 38, pp 3879–3901, 1973.*
Albe–Fessard, et al., "Comparison of Different Animal Models of Chronic Pain"; In *Advances in Pain Research and Therapy*; 13:11–27 (1990) (Raven Press, Ltd., New York).
*Antiepileptic Drugs*, 4$^{th}$ eds., pps. 1–11 (Raven Press, Ltd.., New York 1995).
Bernasconl, et al., "Biochemical Aspects of the Mechanism of Action of Valproate"; In *Anticonvulsants in, Affective Disorders*; 14–32 (1984) (Elsevier Science Publishers B.V.; .Amsterdam, The Netherlands).
Bertman and Adkovat, "Comparison of the Antinociceptive and Antispastic Action of (–)–baclofen After Systemic and Intrathecal Administration in Intact, Acute and Chronic Spinal Rats"; *Brain Res.* 684:8–18 (1995) (Elsevier Science B.V.,).

Casey, *Pain and Central Nervous System Disease* (1991) (Raven Press, Ltd., New York).
Cedarbaum & Schleifer, "Drugs for Parkinson's Disease, Spasticity and Acute Muscle Spasms", In *Goodman & Gilman's The Pharmacological Basis of Therapeutics*, 8$^{th}$ ed. 463–484 (1990) (Pergamon Press, New York).
Chen, et al., "The Adrenergic Agonist Tizanidine Has Differential Effects On Flexor Reflexes of Intact and Spinalized Rat"; *Neuroscience* 23:641–647 (1987) (Pergamon Journals, Ltd., Great Britain).
Costall, et al., "Stereotyped Behaviour Patterns & Hyperactivity Induced by Amphetamine & Apomorphine After Discrete 6–Hydroxydopamine Lesions of Extrapyramidal and Mesolimbic Nuclei"; *Brain Res.* 123:89–111 (1977) (Elsevier/North Holland Biomedical Press, The Netherlands).
Danek, et al., "Restless Leg Syndrome"; In *Neurological Disorders: Course and Treatment*; 819–823 (1996) (Academic Press, Inc.).
Dichter, et al., "New Antiepileptic Drugs"; *Drug Therapy Review Article, The New England Journal of Medicine*, No. 24; 334:1583–1590, (1996).
Dunham, et al., "A Note on a Simple Apparatus for Detecting Neurological Deficit in Rats and Mice"; *J. Am. Pharm. Assoc.* 46:208–209 (1957).
Emrich, et al., "The Use of Sodium Valproate, Carbamazepine and Oxcarbazepine in Patients with Affective Disorders"; *J. Affective Disorders* 8:243–250 (1985) Elsevier Science Publishers B.V. (Biomedical Division).
Feldman, et al., Spasticity—Disordered Motor Control (1980) (Ciba–Geigy Corporation).
Fingl, et al., In *The Pharmacological Basis of Therapeutics*, (1995) 5$^{th}$ ed., Ch. 1, p. 1, MacMillan Publishing Co.,. Inc., NY.

(List continued on next page.)

* cited by examiner

Primary Examiner—Shailendra Kumar

(57) ABSTRACT

Bis(Fluorophenyl)alkylamides have been chemically synthesized which possess beneficial pharmacological properties (e.g., anticonvulsant activity) useful for the treatment of neurological diseases or disorders, such as, for example, epilepsy, convulsions, and seizure disorders. The preferred compounds of the invention also cause little sedation and have high therapeutic and protective indices in animal models of epilepsy. These compounds further possess long pharmacological half-lives, which, in practical clinical therapeutic application, should translate into once-a-day dosing, of great benefit to patients suffering from these diseases and/or disorders. These compounds may also be of further clinical utility in the treatment of other diseases and disorders of the central and peripheral nervous systems, or diseases or disorders affected by them, including, but not limited to, spasticity, skeletal muscle spasms and pain, restless leg syndrome, anxiety and stress, and bipolar disorder.

19 Claims, 8 Drawing Sheets

OTHER PUBLICATIONS

Foye, et al., "Anticonvulsants", *Principles of Medicinal Chemistry* 4$^{th}$ ed. 182–198 (1995) (Williams & Wilkins, PA).

Foye, "Anticonvulsants" *Principles of Medicinal Chemistry*, 3$^{rd}$ ed. (1989) 173–178 (Lea & Febiger, PA).

Hering and Kuritzky, "Sodium Valproate in the Prophylactic Treatment of Migraine, a Double Blind Study Versus Placebo" 12:81–84 (1992) *Cephalalgia*.

Hering and Kurtizky "Sodium Valproate in the Treatment of Cluster Headache": (1989) Loc. Cit. 9:195–198 *Cephalalgia*.

Irwin, "Comprehensive Observational Assessment":"Ia. A Systematic, Quantitative Procedure for Assessing the Behavioral and Physiologic State of the Mouse" *Psychopharmacologia* 13:222–257 (1968).

Kupferberg, "Antiepileptic Drug Development Program: A Cooperative Effort of Government and Industry"; *Epilepsia* 30 (Suppl 1) S51–S56 (1989) (Raven Press, Ltd., New York).

Lee, et al. "Peripheral GABA$_A$ Receptor–Mediated Effects of Sodium Valproate on Dual Plamsa Protein Extravasation to Substance P and Trigeminal Stimulation" 116:1661–1667 (1995) *Brit. J. Pharmacol.* (Stockton Press).

Lloyd and Morselli, in *Psychopharmacology: The Third Generation of Progress* (Raven Press 1987).

Loscher and Schmidt, "Strategies in Antiepileptic Drug Development: Is Rational Drug Design Superior to Random Screening and Structural Variation?" *Epilepsy Research*, 17::95–134 (1994) (Elsevier Science B.V.).

Mathew and Sabiha, "Valproate in the Treatment of Persistent Chronic Daily Headache. An Open Label Study." *Headache*, 31:71–74 (1991).

Mellick and Mellick, *Neurology* 45 (suppl.) 285–286 (1995).

*Merk Index*, 12$^{th}$ ed., Merck & Co., Inc., Rahway, NJ 1996.

McNamara, "Drugs Effective in the Therapy of the Epilepsies" In *Goodman and Gilman's The Pharmacological Basis of Therapeutics*, 9$^{th}$ ed. (1996) 461–486 (McGraw–Hill, New York).

O'Keefe, "Restless Legs Syndrome", *Arch. Intern. Med.* 156:243–248 (1996).

Olson, et al., "Gabapentin for Parkinsonism, A Double–Blind, Placebo–controlled, Crossover Trial" *Am. J. Med.*, 102:60–66 (1997) (Excerpta Medica, Inc.).

Remington's *Pharmaceutical Sciences*, 18$^{th}$ ed. (1990) (Mack Publishing, PA).

Sachdev, et al., "Restlessness, the Anatomy of a Neuropsychiatric Symptom" *Austral. New Zealand J. Psychiatry* 30:38–53 (1996).

Swerdlow, "Anticonvulsant Drug and Chronic Pain", *Clinical Neuropharmacology*, 7:51–82 (1984) (Raven Press, New York).

White, et al., "Experimental Selection, Quantification, and Evaluation of Antiepileptic Drugs", *Antiepileptic Drugs*, 4$^{th}$ ed. 99–110 (1995) (Raven Press, Ltd., New York).

Wolf, M.E., "Drug Allergy", *Burger's Medicinal Chemistry and Drug Discovery*, 5$^{th}$ ed. 182–198 (1986) (A Wiley–Interscience Publication, New York).

| COMPOUND# | FRINGS SEIZURE SUSCEPTIBLE MOUSE (mg/kg p.o.) | M.E.S. (mouse, mg/kg i.p.) (rat, mg/kg p.o.) | STRUCTURE |
|---|---|---|---|
| 1 | $ED_{50}$ =51.8<br>$TD_{50}$ =~1500<br>$^aP.I.$=~29 | MOUSE: $ED_{50}$ =36 mg/kg i.p.<br>RAT: $ED_{50}$ =46 mg/kg p.o. | (3-F-C6H4)2CH-CH2-C(O)-NH2 |
| 2 | $ED_{50}$ =8.0(6.2-10.6)<br>$TD_{50}$ =>1000(2/6)<br>P.I.=>125 | MOUSE: 3/3 PROTECTED AT 100 mg/kg i.p.<br>RAT: 3/4 PROTECTED AT 30 mg/kg p.o. | (3-F-C6H4)2CH-CH2-C(O)-NH-CH3 |
| 3 | $ED_{50}$ =60.6<br>$TD_{50}$ =>1000<br>P.I.=>16.5 | NOT TESTED | (3-F-C6H4)2CH-CH2-C(O)-NH-CH2CH3 |
| 4 | INACTIVE UP TO 300 | NOT TESTED | (3-F-C6H4)2CH-CH2-C(O)-NH-CH(CH3)2 |
| 5 | MARGINAL ACTIVITY AT 300 | NOT TESTED | (3-F-C6H4)2CH-CH2-C(O)-NH-C(CH3)3 |
| 6 | INACTIVE UP TO 300 | NOT TESTED | (3-F-C6H4)2CH-CH2-C(O)-NH-CH(CH3)CH2OH |

$^aP.I.$ = $TD_{50}/ED_{50}$; $TD_{50}$ WAS DETERMINED BY IMPAIRMENT OF PERFORMANCE IN ROTAROD TESTING

FIG. 1A

| | | | |
|---|---|---|---|
| 7 | $ED_{50}=157$<br>$TD_{50}=\sim1000(2/4)$<br>$P.I.=\sim6.4$ | MOUSE: 3/3 PROTECTED AT 100 mg/kg i.p.<br>RAT: 2/4 PROTECTED AT 30 mg/kg p.o. | 3-F-C₆H₄–CH(3-F-C₆H₄)–CH₂–C(=O)–NH–CH₂CH₂OH |
| 8 | $ED_{50}=36.3$<br>$TD_{50}=>1000$<br>$P.I.=>27.6$ | NOT TESTED | 3-F-C₆H₄–CH(3-F-C₆H₄)–CH₂–C(=O)–N(CH₃)₂ |
| 9 | $ED_{50}=84.6$<br>$TD_{50}=>1000(2/6)$<br>$P.I.=>11.8$ | NOT TESTED | 3-F-C₆H₄–CH(3-F-C₆H₄)–CH₂–C(=O)–N(CH₂CH₃)₂ |
| 10 | $ED_{50}=23.3$<br>$TD_{50}>1000$<br>$P.I.>43$ | MOUSE: $ED_{50}=63.5$ mg/kg i.p.<br>RAT: $ED_{50}=17.2$ mg/kg p.o. | 4-F-C₆H₄–CH(4-F-C₆H₄)–CH₂–C(=O)–NH₂ |
| 11 | $ED_{50}=35.7(23-52.2)$<br>$TD_{50}=>100$<br>$P.I.=>3$ | MOUSE: 3/3 PROTECTED AT 100 mg/kg i.p.<br>RAT: 1/4 PROTECTED AT 30 mg/kg p.o. | 3-F-C₆H₄–CH(3-F-C₆H₄)–CH₂CH₂–C(=O)–NH₂ |
| 12 | $ED_{50}=8$<br>$TD_{50}>500(2/6)$<br>$P.I.>62$ | MOUSE: 3/3 PROTECTED AT 100 mg/kg i.p.<br>RAT: $ED_{50}=9.6$ mg/kg p.o. | 4-F-C₆H₄–CH(4-F-C₆H₄)–CH₂CH₂–C(=O)–NH₂ |

FIG. 1B

| | | | |
|---|---|---|---|
| 13 | $ED_{50}$=21.6<br>$TD_{50}$>1000(2/6)<br>P.I.>46.3 | MOUSE: 3/3 PROTECTED AT 100 mg/kg i.p.<br>RAT: 2/4 PROTECTED AT 30 mg/kg p.o. | [structure: 3,3-bis(4-fluorophenyl)-N-methylpropanamide] |
| 14 | $ED_{50}$=70.9<br>$TD_{50}$>1000(1/6)<br>P.I.>14.1 | MOUSE: INACTIVE AT 100 mg/kg i.p.<br>RAT: INACTIVE AT 30 mg/kg p.o. | [structure: 2,2-bis(4-fluorophenyl)-N-methylacetamide] |
| 15 | $ED_{50}$=113.7<br>$TD_{50}$>1000(1/4)<br>P.I.>8.7 | NOT TESTED | [structure: 3,3-bis(4-fluorophenyl)-N,N-diethylpropanamide] |
| 16 | NOT TESTED | MOUSE: 1/1 PROTECTED AT 30 mg/kg i.p.<br>RAT: 2/4 PROTECTED AT 30 mg/kg p.o. | [structure: 2,2-bis(4-fluorophenyl)acetamide] |
| 17 | NOT TESTED | MOUSE: $ED_{50}$=90.7 mg/kg i.p.<br>RAT: $ED_{50}$=>>30 mg/kg p.o. | [structure: 3,3-bis(3-fluorophenyl)propanoic acid] |
| 18 | NOT TESTED | NOT TESTED | [structure: 3,3-bis(4-fluorophenyl)propanoyl glycinamide] |

FIG. 1C

| FIG. 2A | FIG. 2B | FIG. 2C |

*p<0.05 COMPARED TO VEHICLE-TREATED

COMPOUND 1 AND BACLOFEN ELICIT A REDUCTION IN THE FLEXOR REFLEX IN NORMAL ANESTHETIZED RATS.

ANTICONVULSANT AND CENTRAL NERVOUS SYSTEM-DEPRESSING BIS (FLUOROPHENYL)ALKYLAMIDES AND THEIR USES

RELATED APPLICATIONS

This application is a Continuation of International Application No. PCT/US98/26315, filed Dec. 9, 1998 which claims the benefit of Provisional Application No. 60/069,005, filed Dec. 10, 1997.

FIELD OF THE INVENTION

The present invention relates to compounds useful in treating pathological conditions, such as convulsions and spasticity, without producing undesirable excessive sedation or muscle weakness in animal subjects, including humans. More particularly, the invention relates to the preparation, biological activities, and therapeutic uses of 3,3-bis(3-fluorophenyl)propionamide and related compounds in patients suffering from pathologies of this nature.

BACKGROUND OF THE INVENTION

The following is a description of relevant art, none of which is admitted to be prior art to the claims.

A number of pathological states, diseases, and disorders are characterized by a profound aberration in the normal function of the central nervous system (CNS). Such conditions include multiple sclereosis, strokes, spinal cord injuries, chronic neurodegenerative disorders and diseases such as Parkinson's and Huntington's diseases, Alzheimers disease, amyotrophic lateral sclerosis (ALS; Lou Gehrig disease), and epilepsy. At the clinical level, these states usually only respond to pharmacologic intervention with compounds or substances that possess significant activity at the level of the CNS.

Because of the availability of reasonably predictive and experimentally accessible animal models of convulsant states, a number of clinically useful anticonvulsants have been prepared and developed in the 20th century, many from compounds originally developed as sedative-hypnotic or anxiolytic agents. In current medical practice, many of the compounds in clinical use for the symptomatic treatment of spasticity are various kinds of central muscle relaxants, usually having been first developed for the treatment of other clinical indications. Most of these medical agents are fraught with undesirable, troublesome, and poorly tolerated side effects in the treatment of spastically, and all are far from being ideal clinical entities in this application (MERCK INDEX, 12$^{th}$ ed., Merck & Co., Rahway, N.J., 1996).

Similarly, many anticonvulsants and antispastics in clinical use are plagued by the occurrence of significant side effects which limit their long-term clinical utility, including troublesome daytime sedation (drowsiness, cognitive blunting, and/or "hangover"), muscular weakness, tolerance, gingivitis and gum recession (gingival hyperplasia), and potentially fatal blood dyscrasias and hepatotoxicities (some of which are or can be fatal). Among these agents are the benzodiazepines, which can cause cognitive blunting. Other agents, such as valproate and phenyltoin (Dilantin) can cause or produce hepatotoxicity and gingival hyperplasia, respectively, among other side effects limiting their therapeutic potential. Many of these side effects are especially troubling in the clincial treatment of pediatric epilepsy (or epilepsy in children). Thus, there is a clear and persistent need for the development of new clinical entities with improved side effect profiles and efficacy for the treatment of convulsive states or conditions.

In addition, there is a need for the development of new clinical entities with improved side effect profiles and efficacy for the treatment of spasticity and epilepsy. Certain bis(fluorophenyl) alkylamides, are described in U.S. Ser. No. 08/873,011, filed Jun. 11, 1997, which is commonly owned with the present invention, and is hereby incorporated herein by reference in its entirety.

SUMMARY OF THE INVENTION

Accordingly, it is an object of the present invention to provide compounds and a novel therapeutic approach for the treatment of various pathologies by effecting a modulation in CNS activity without producing excessive sedation, muscle weakness, fatigue, gingival hyperplasia, blood dyscrasias, or hepatotoxicity.

It also is an object of the present invention to provide a method for alleviating one or more symptoms associated with a condition, such as convulsions and spasticity, that is ameliorated by means of modulating CNS activity.

It is another object of the present invention to provide a novel anticonvulsant therapy.

In accomplishing these and other objectives, there has been provided, according to one aspect of the present invention, a use of a novel compound selected from the group consisting of 3,3-bis(3-fluorophenyl)propanamide and structurally related bis(fluorophenyl)alkylamides and acids (see, the example, FIGS. 1 and 2) in the preparation of a pharmaceutical formulation or composition for use in a method of treating a pathology that is ameliorated by a modulation of CNS activity, whereby at least one symptom of said pathology is alleviated. Thus, the present invention also contemplates a treatment method comprising the step of administering, to a patient suffering from a pathology that is ameliorated by a modulation of CNS activity, a therapeutically effective amount of a pharmaceutical formulation comprising a pharmaceutically acceptable carrier and a novel composition selected from the aforementioned group of agents.

Pursuant to one embodiment of the invention, the treated pathology is convulsions, an affective mood disorder, such as bipolar mood disorder, a neuropathic pain syndrome, a headache, such as a migraine headache, or a restlessness syndrome. For another embodiment, the pathology in question is ameliorated by a centrally mediated decrease in muscle tone, and is illustrated by spasticity.

In accordance with another aspect of the present invention, a use is provided for the novel compositions of matter comprising 3,3-bis(3-fluorophenyl)propanamide and structurally related amide and acid compounds in the preparation of a pharmaceutical formulation for use in a method of treating a symptom of spasticity. By the same token, the present invention provides a method for alleviating a symptom of spasticity in a subject in need of such treatment, comprising the step of administering a therapeutically effective amount of one of the novel compositions as described above.

Thus, in a preferred embodiment of the invention, a compound is provided having the formula

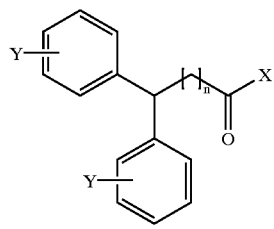

wherein:
Y is independently selected from the group consisting of —H, —F, and —Cl;
X is either —NR$^1$R$^2$ or —OR$_1$;
R$^1$ is selected from the group consisting of —H, alkyl, and hydroxyalkyl;
R$^2$ is selected from the group consisting of —H, methyl, and ethyl;
and n is either 0, 1, 2, 3, or 4. Preferably, R$^1$ is selected from the group consisting of —H, methyl, ethyl, isopropyl, isobutyl, tert-butyl, hydroxyisopropyl, and hydroxyethyl.

Thus, in another preferred embodiment of the embodiment of the invention, a compound is provided having the formula

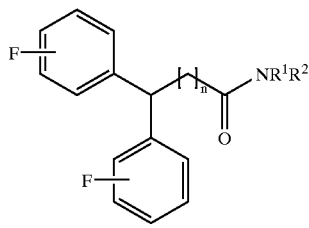

wherein:
each F is independently in either the meta- or para- position;
R$^1$ is selected from the group consisting of —H, alkyl, and hydroxyalkyl;
R$^2$ is selected from the group consisting of —H, methyl, and ethyl;
and n is 0, 1, 2, 3, or 4. Preferably, R$^1$ is selected from the group consisting of —H, methyl, ethyl, isopropyl, isobutyl, tert-butyl, hydroxyisopropyl, and hydroxyethyl.

In a more preferred embodiment, a compound is provided having the formula

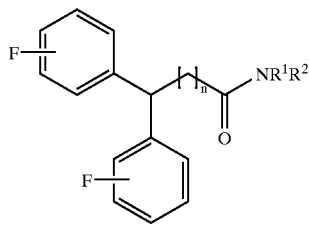

wherein
n is 0, 1, or 2;
both F are either in the meta- or para- position;
R$^1$ is selected from the group consisting of —H, alkyl, and hydroxyalkyl; and R$^2$ is selected from group consisting of —H, methyl, and ethyl. More preferably, R$^2$ is —H. More preferably, said compound is selected from the group consisting of compound 1, 2, 3, 7, 8, 9, 10, 11, 12, 13, 14, and 15. In most preferred embodiments, said compounds is Compound 1.

In other preferred embodiment of the invention, a method is provided for treating a patient having a neurological disease or disorder comprising administering a compound of the formula

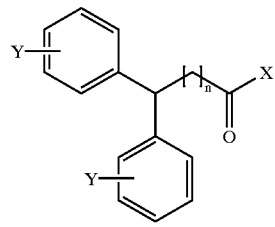

wherein:
Y is independently selected from the group consisting of —H, —F, and —Cl;
X is either —NR$^1$R$^2$ or —OR$^1$;
R$^1$ is selected from the group consisting of —H, alkyl, and hydroxyalkyl;
R$^2$ is selected from the group consisting of —H, methyl, and ethyl;
and n is either 0, 1, 2, 3, or 4. Preferably, R$_1$ is selected from the group consisting of —H, methyl, ethyl, isopropryl, isobutyl, tert-butyl, hydroxyisopropyl, and hydroxyethyl.

Thus, in another preferred embodiment of the invention, a method is provided for treating a patient having a neurological disease or disorder comprising administering a compound of the formula

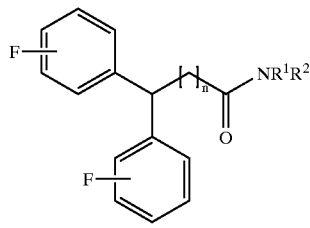

wherein:
each F is independently in either the meta- or para- position;
R$^1$ is selected from the group consisting of —H, alkyl, and hydroxyalkyl;
R$^2$ is selected from the group consisting of —H, methyl, and ethyl;
and n is 0, 1, 2, 3, or 4. Preferably, R$^1$ is selected from the group consisting of —H, methyl, ethyl, isopropyl, isobutyl, tert-butyl, hydroxyisopropyl, and hydroxyethyl.

In a more preferred embodiment, a method is provided for treating a patient having a neurological disease or disorder comprising administering a compound of the formula

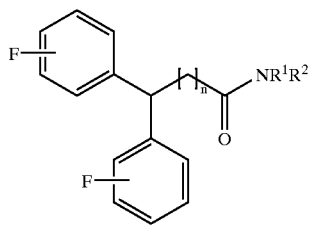

wherein:
n is 0, 1, or 2;
both F are either in the meta- or para- position;
$R^1$ is selected from the group consisting of —H, alkyl, and hydroxyalkyl; and
$R^2$ is selected from the group consisting of —H, methyl, and ethyl. More preferably, $R^2$ is —H. More preferably, the compound is selected from the group consisting of Compound 1, 2, 3, 7, 8, 9, 10, 11, 12, 13, 14, and 15. In most preferred embodiments, and compound is Compound 1.

in other preferred methods, the neurological disease or disorder is selected from the group consisting of epilepsy, convulsions, and seizure disorders. In other preferred aspects, the treating of the patient alleviates or prevents convulsions in said patient. In other preferred aspects, the neurological disease or disorder is associated with spasticity. In other preferred aspects, the neurological disease or disorder is a neurodegenerative disorder. Preferably, said neurological disease or disorder is selected from the group consisting of spasticity, skeletal muscle spasms, restless leg syndrome, anxiety, stress, multiple sclerosis, stroke, head trauma, spinal cord injury, Parkinson's Disease, Huntington's Disease, Alzheimers Disease, amyotrophic lateral sclerosis, migraine, headaches, and bipolar disorder.

Other preferred embodiments of the invention include methods of alleviating or preventing spasticity, or one or more symptoms of spasticity, in a patient, comprising administering a compound of the invention.

Also provided are pharmaceutical compositions, comprising a compound of the invention, and a pharmaceutically acceptable carrier. Preferably, the pharmaceutical composition comprises a compound selected from the group consisting of Compounds 1, 2, 3, 7, 8, 9, 10, 11, 12, 13, 14, and 15, and a pharmaceutically acceptable carrier. More preferably, the pharmaceutical composition comprises Compound 1.

Also provided in the present invention is a method for making a therapeutic agent comprising the steps of screening for said agent by determining whether said agent alleviates spasticity, and synthesizing said therapeutic agent in an amount sufficient to provide said agent in a therapeutically effective amount to a patient. Preferably, the therapeutic agent comprises a compound of the invention.

Also provided in the present invention is a method for modulating CNS activity comprising administering to a patient a compound of the invention. Preferably, said modulation of CNS activity alleviates a symptom associated with convulsions, spasticity, an affective mood disorder, a neuropathic pain syndrome, a headache, a restlessness syndrome, or a movement disorder.

other objects, features, and advantages of the present invention will become apparent from the following detailed description. It should be understood, however, that the detailed description and the specific examples, while indicating preferred embodiments of the present invention, are given by way of illustration only since various changes and modifications within the spirit and scope of the invention will become apparent to those skilled in the art from this detailed description.

BRIEF DESCRIPTION OF THE DRAWINGS

Figures 1, 1A, 1B, 1C:
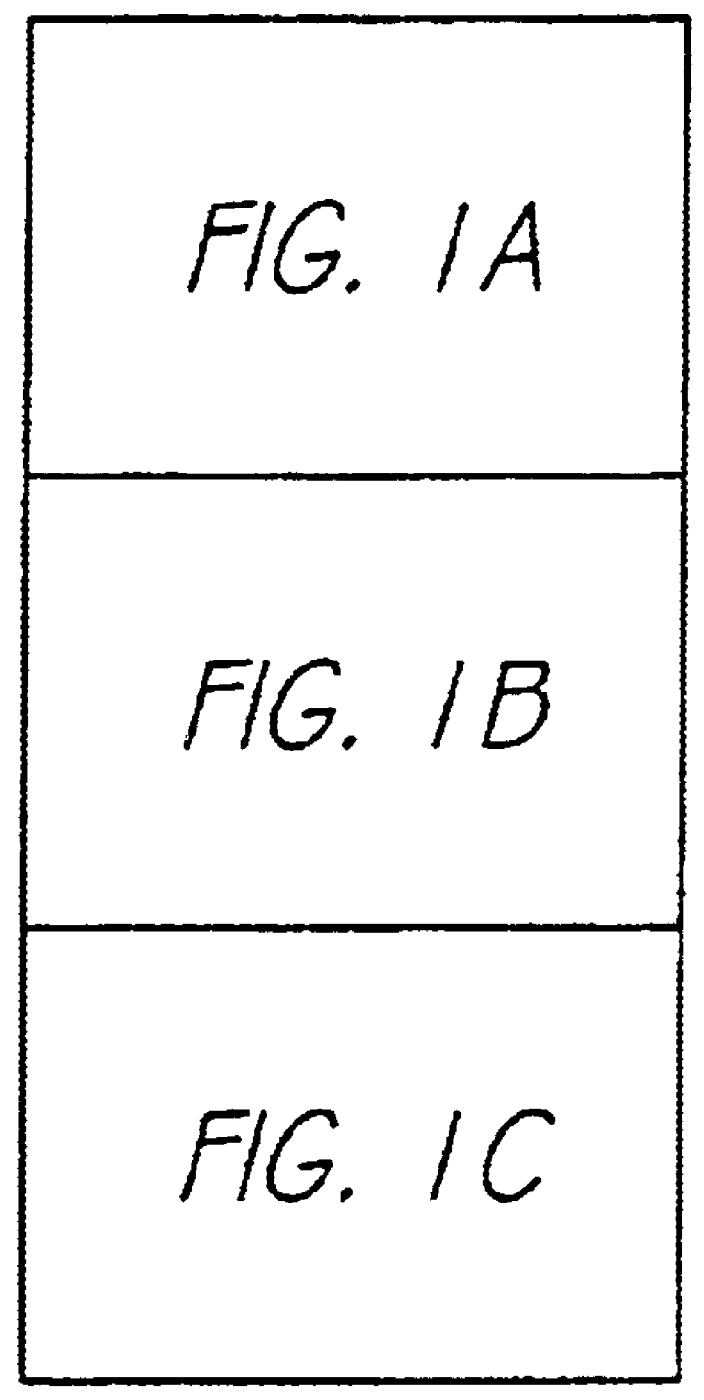

FIG. 1 depicts the structure and in vivo anticonvulsant activities as assayed using the methods described herein, of 3,3-bis(3-fluorophenyl)propanamide and several of its substituted analogs and congeners.

DETAILED DESCRIPTION OF THE PREFERRED EMBODIMENT

1. OVERVIEW

Figures 2, 2A:
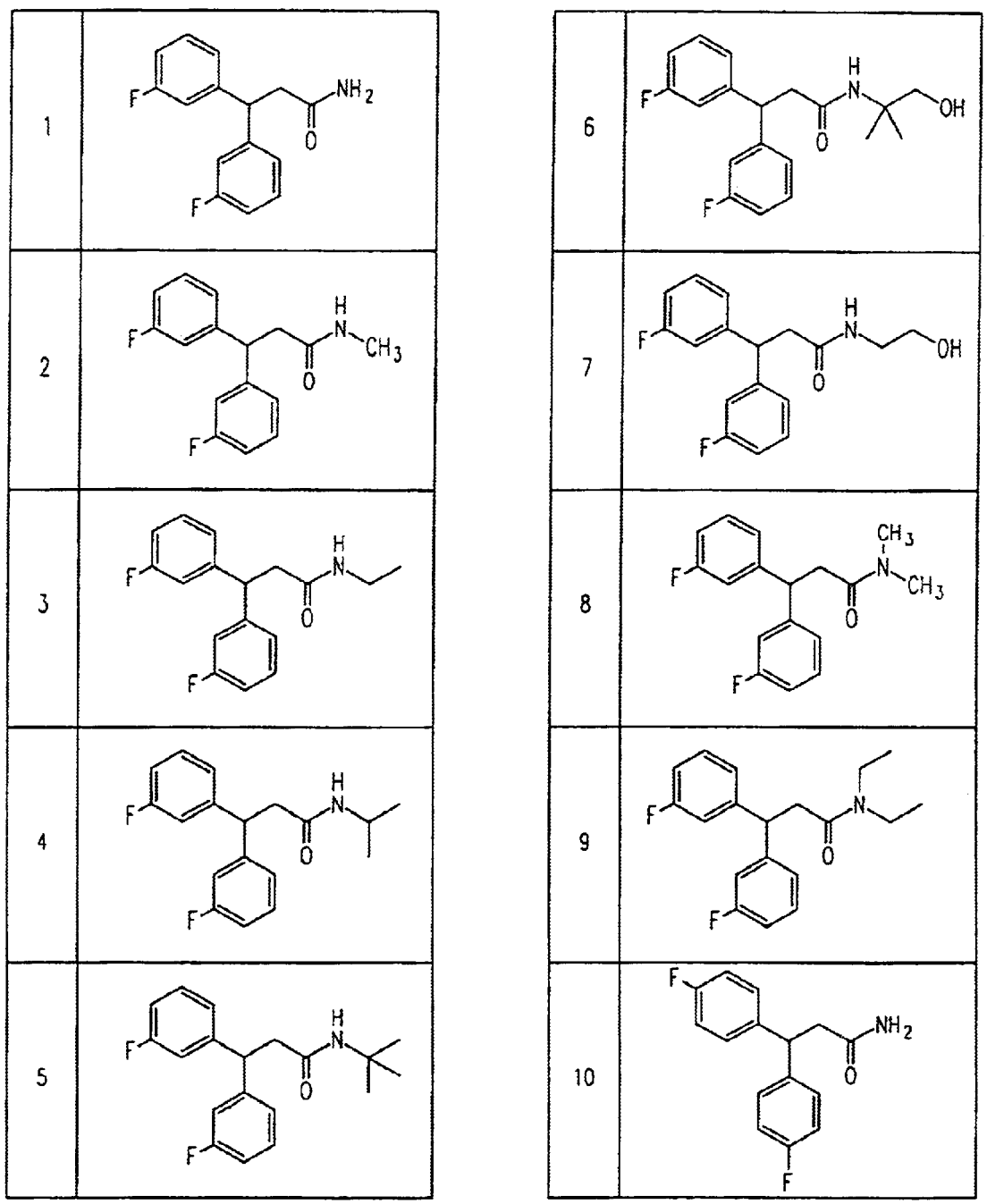
FIG. 2 depicts the structures of 3,3-bis(3-fluorophenyl) propanamide and additional analogs and cogeners.
Figure 2B:
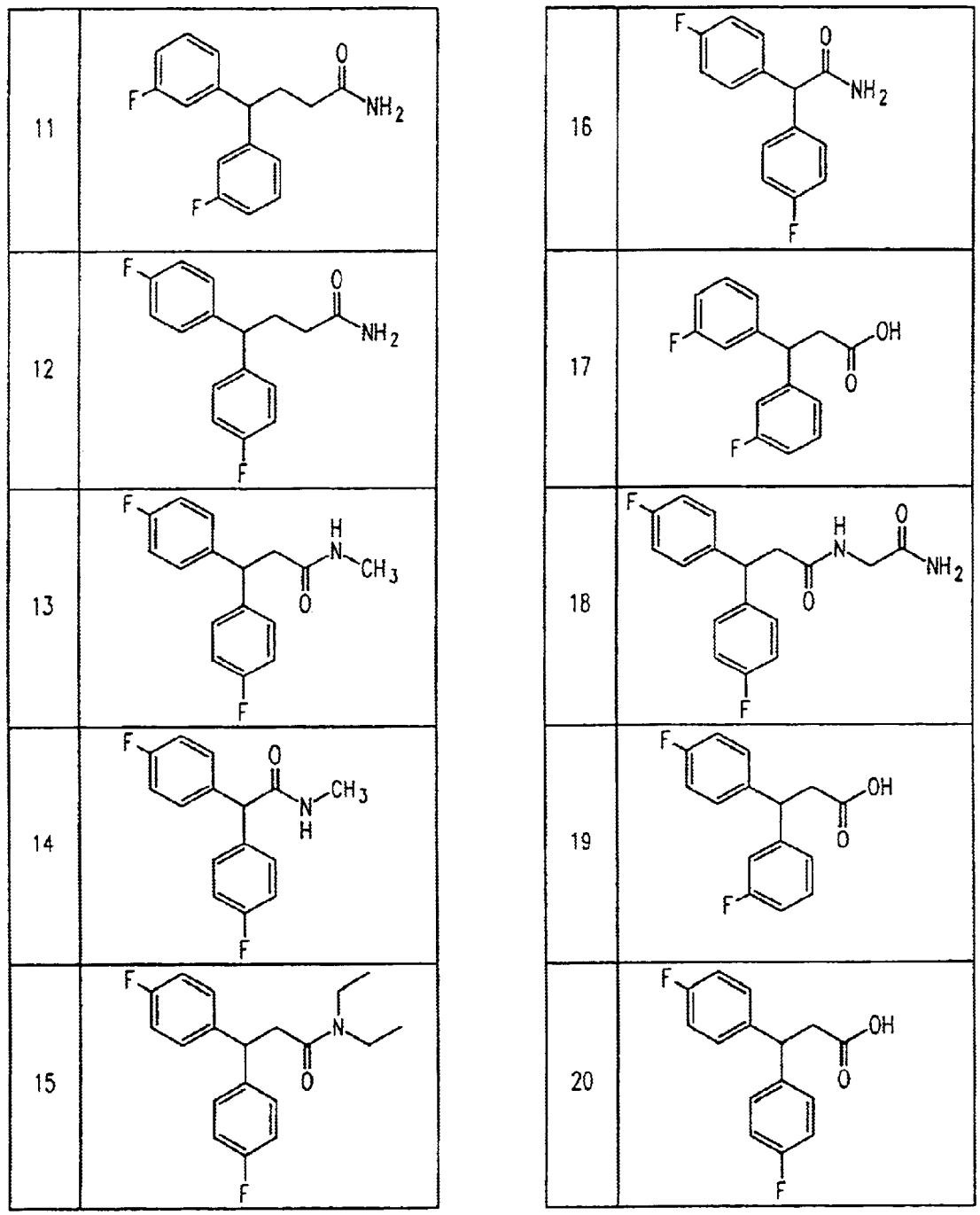
Figure 2C:
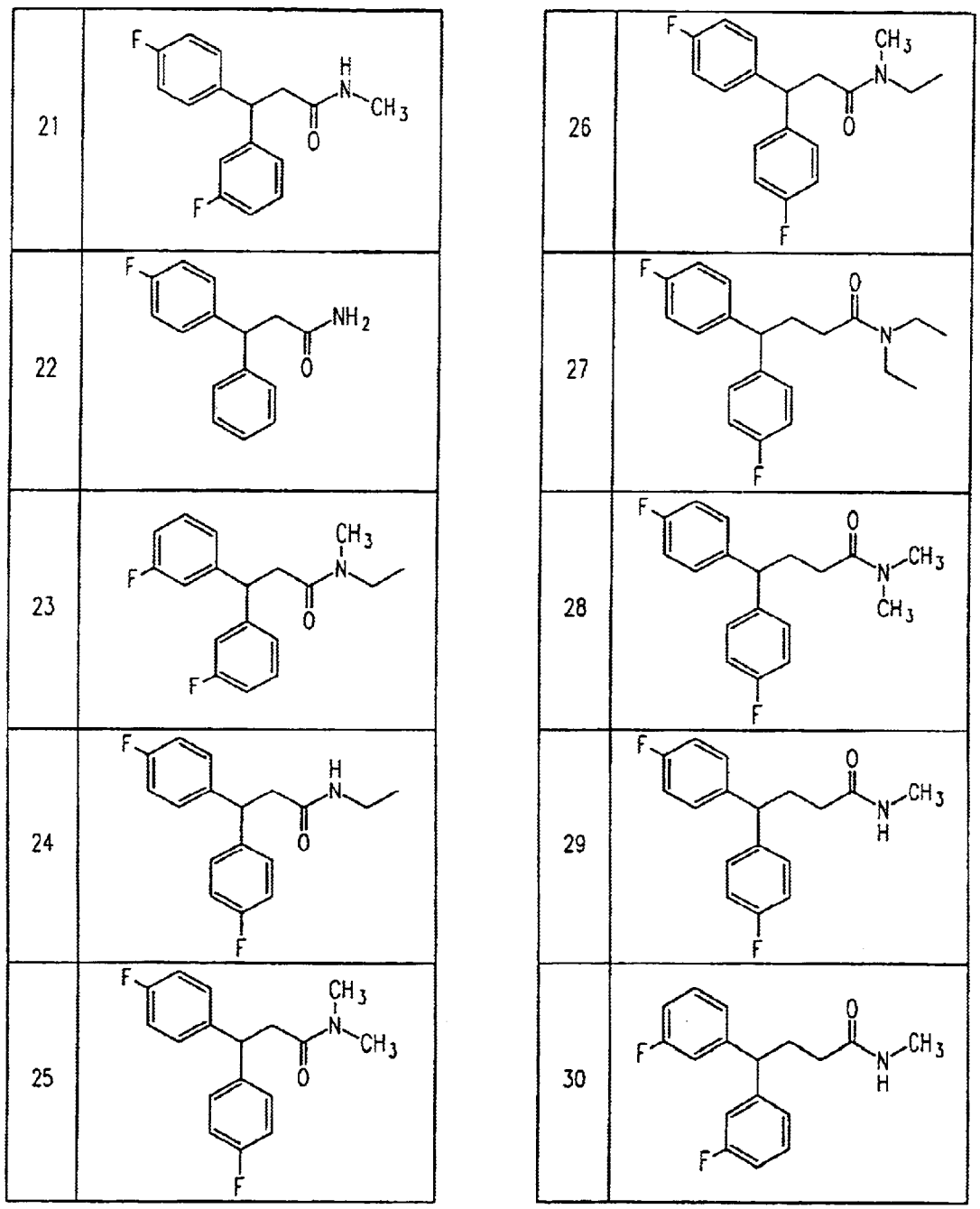
Figure 3:
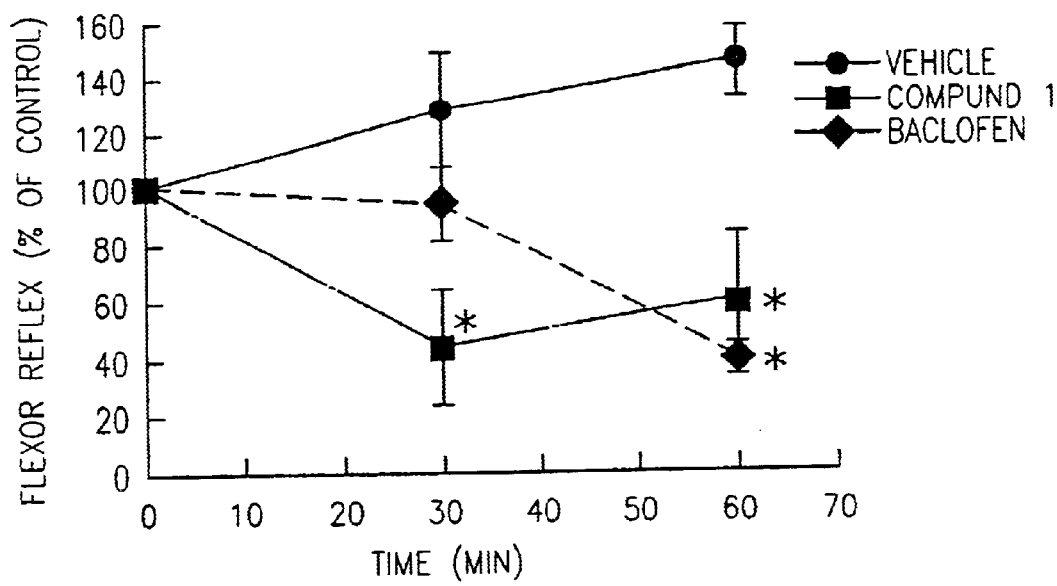
FIG. 3 depicts the reduction in the flexor reflex in normal anesthetized rats elicited by Compound 1 in comparison to baclofen, as assayed using the methods described herein.

The inventors have discovered that 3,3-bis(3-fluorophenyl)propanamide and certain of its pharmacologically active analogs and congeners can be administered in vivo to effect a modulation of CNS activity. That is, these agents modulate CNS activity, by enhancing inhibitory, or decreasing excitatory, neurotransmission centrally, without complete suppression of all activity. Pursuant to the present invention, therefore, a subject who receives such an agent is not overtly sedated, anesthetized, or paralyzed in the context of, for example, decreasing seizures (no anesthesia), decreasing muscle tone (no paralysis), eliciting a calmative effect (no sedation), or ameliorating an ambulatory syndrome such as spasticity (no weakness or flaccidity).

A number of pathologies, exemplified by convulsions (seizures), spasticity, affective mood disorders, such as bipolar mood disorder, headaches (chronic, cluster, migraine), restlessness syndromes, neuropathic pain, and movement disorders, have at least one symptom that is alleviated by a modulation of CNS activity. Accordingly, an individual who suffers from such a pathology is a candidate for therapy that entails, pursuant to the present invention, the individuals's receiving a pharmaceutical formulation or composition containing 3,3-bis(3-fluorophenyl)propanamide or one of its structurally related analogs or congeners as one of the principal active ingredients.

2. EXEMPLARY PATHOLOGIES AMELIORATED BY A MODULATION OF CENTRAL NERVOUS SYSTEM (CNS) ACTIVITY

CONVULSIONS: Epilepsy is a common disorder which has many causes, and it can be very difficult to control clinically, often requiring treatment for many years to keep seizures under control. Researchers have state that "[a]t this time, there is no satisfactory treatment for epilepsy in a substantial proportion of patients. Clinical trials have shown that certain patients have a better response to one drug than another, even when the patients have similar types of seizures and the drugs have similar mechanisms of action. The frequency and severity of side effects also varies substantially. Thus, multiple medications with different mechanisms of action and attendant side effects will be needed for treatment of epilepsy until either epilepsy can be cured or a potent, safe new drug with broad activity is discovered" and developed. Dichter et al., *Drug Therapy* 334:1583 (1996).

Due to the widespread availability of reasonably predictive and experimentally accessible animal models of convulsant states, a number of clincially useful anticonvulsants have been prepared and developed. For example, see Cereghino et al., "Introduction," in ANTIEPILEPTIC DRUGS, 4th ed., pages 1–11 (Rave Press 1995), which states: "In many patients, seizures can be controlled with currently available antiepileptic drugs, but 25 to 30 percent of patients continue to have seizures despite optimal therapy, while many others experience unacceptable side effects." Dichter et al. (1996) supra.

Thus, many anticonvulsants in clincial use are plagued by the occurrence of significant side effects, including troublesome daytime sedation, muscular weakness, tolerance, gingival hyperplasia, and potentially fatal blood dyscrasias and hepatotoxicity. Many of these side effects are especially of concern in the clinical management (treatment) of epilepsy in children.

The present invention can be used to treat convulsive disorders such as epilepsy. That is, the compositions and pharmaceutical formulations and compositions of the invention display "anticonvulsant activity," which is evidenced by a reduction of the severity, number, or duration of convulsions in animal models of epilepsy. To alleviate convulsions includes reducing the severity, number of duration of convulsions in a patient. Accordingly, the novel compositions and pharmaceutical formulations and compositions should be useful in treating conditions such as, but not limited to, generalized tonic-clonic seizures, absence seizures, myoclonic seizures, simple partial seizures, complex partial seizures, secondarily generalized partial seizures, status epilepticus, and trauma-induced seizures, as occur following head injury or surgery.

SPASTICITY: Spasticity is a disorder characterized by an increase in tonic stretch reflexes (muscle tone) with exaggerated tendon jerks resulting from hyperexcitability of the stretch reflex. Lance, Symposia synopsis, in SPASTICITY—DISORDERED MOTOR CONTROL, Feldman et al. (Eds. (1980). Major disease states and conditions associated with spasticity include multiple sclerosis, cerebral palsy, stroke, trauma or injury to the spinal cord, and head trauma. Symptoms that occur with spasticity include painful flexor and extensor spasms, increased or exaggerated deep-tendon reflexes, clonus, muscular weakness, fatigue, lack of dexterity, various degrees of loss of general motor function, paralysis, and impairment of sleep.

The pathological states observed in spasticity are fundamentally different at the physiological level from the commonly experienced acute muscular aches, strains, and sprains that occur from a localized external insult to a particular muscle, i.e., outside of or peripheral to the CNS. These pathological states also are different from the relatively common involuntary spasms or smooth muscle, such as vasuclar spasms, bladder spasms, and bronchial spasms. Such non-spastic (non-CNS), peripheral or localized symptoms are commonly treated with so-called "antispasmodic" or "spasmolytic" agents, but these generally are not useful in treating spasticity. Cedarbaum & Schleifer, "Drugs for Parkinson's Disease, Spasticity and Acute Muscle Spasms," in GOODMAN AND GILMAN'S THE PHARMACOLOGICAL BASIS OF THERAPEUTICS, 8th ed. [hereafter GOODMAN AND GILMAN'S], pages 463–484 (Pergamon Press 1990).

The compositions of matter and pharmaceutical formulations and compositions employed in accordance with the present invention can effect a centrally mediated decrease in muscle tone and, hence, are useful for the acute or chronic alleviation of one or more symptoms or side effects of spasticity. In this context, "spasticity" refers to a heightened tone of skeletal muscle with is manisfested by symptoms such as, but not limited to, painful flexor or extensor spasms, increased or exaggerated deep-tendon reflexes, hyperreflexia, loss of dexterity, muscular weakness, exaggerated tendon jerks, and clonus. The phrase "antispasticity agent" refers here to a composition that is useful for the symptomatic treatment of spasticity, as demonstrated by the alleviation of at least one of the following manisfestations or side effects of spasticity: painful flexor or extensor spasms, increased or exaggerated deep-tendon reflexes, hyperreflexia, loss of dexterity, muscular weakness, exaggerated tendon jerks, and clonus, or the reduction of the frequency of these manisfestations or side effects.

Accordingly, the "alleviation" of spasticity refers here to the lessening of one or more symptoms of spasticity, including, but not limited to, painful flexor or extensor spasms, increased or exaggerated deep-tendon reflexes, hyperreflexia, loss of dexterity, muscle weakness, exaggerated tendon jerks, and clonus, or the reduction of the frequency of these manisfestations or side effects.

AFFECTIVE MOOD DISORDERS: These include conditions ranging from depression to dysphoric mania, for example, mania, schizoaffective disorder, traumatic brain injury-induced aggression, post-traumatic stress disorder, bipolar mood disorder, panic states, and behavioral dyscontrol syndromes, See Emrich et al., *J. Affective Disorders* 8:243–250 (1985) and Bernasconi et al., in ANTICONVULSANTS IN AFFECTIVE DISORDERS, pages 14–32 (Excerpta Medical 1984). The novel compositions and pharmaceutical formulations and compositions according to the present invention are effective in the treatment of these diseases, disorders, and conditions, and should exhibit improved side effect profiles when compared to currently existing therapeutic agents in this therapeutic category.

NEUROPATHIC PAIN SYNDROMES: Conditions in this category, involving "neuropathic pain," affect a significant number of patients suffering from disorders of the brain or spinal cord, such as stroke, trauma, multiple sclerosis, and diabetes. Casey, in PAIN AND CENTRAL NERVOUS SYSTEM DISEASE (Raven 1991). The use of anticonvulsants to treat various pain states has been documented extensively. Swendlow, *J. Clin. Neuropharmacol.* 7: 51–82 (1984). Thus, a novel composition or pharmaceutical formulation or composition of the present invention can be applied in similar fashion to ameliorate neuropathic pain.

HEADACHES: Headaches of the migraine type (Herin and Kuritzky, *Cephalagia* 12:81–84 (1992)), the cluster type (Hering and Kuritzky, *loc. cit.* 9:195–198 (1989)), and the chronic type (Mathew and Sabiha, *Headache* 31: 71–74 (1991)) have been treated with anticonvulsants. The compositions and formulations of the present invention can therefore be used to alleviate the symptoms associated with each of these three headache types, without the adverse side effects of current existing therapies.

RESTLESSNESS SYNDROME: The phrase "restlessness syndrome" denotes a somatic (non-metal) restlessness characterized by involuntary movement of the limbs, as well as by a sense of physical (rather than mental) agitation, which is independent of mood and, hence, is distinguished from restlessness per se. (See Sachev et al., *Austral. New Zealand J. Psychiatry* 30:38–53 (1996)).

Restlessness syndromes, inclusive of numerous indications, can be observed in association with many organic and non-organic psychiatric illnesses. For example, drug-induced restlessness (tardive, chronic, and withdrawal akathisias), such as drug-induced extrapyramidal symptoms, is one of the most common side effects of neuroleptic drug therapy. Also within the restlessness-syndrome rubric are the so-called "restless leg syndrome" and "sleep-related periodic leg movements," pathologies that can be associated with head and/or spinal cord trauma and with lesions of the spinal cord. Idiopathic restless leg syndrome follows an autosomal dominant inheritance, with a variable clinical expression of symptoms. See O'Keefe, Arch. Intern. Med. 156: 243–248 (1996); Danek et al., in NEUROLOGICAL DISORDERS: COURSE AND TREATMENT, pages 819–823 (Academic Press 1996); Mellick and Mellick, Neurology 45(suppl.): 285–286 (1995). The present invention provides an effective therapy for restlessness syndromes with minimal side effects.

MOVEMENT DISORDERS: Various agents are known to decrease the dyskinetic movement characterizing movement disorders such as Parkinson's disease, Huntington's chorea, Alzheimer's disease, tardive dyskinesia, and stiff-man syndrome. Lloyd and Morselli, in PSYCHOPHARMACOLOGY: THE THIRD GENERATION OF PROGRESS (Raven Press 1987). A therapy within the present invention alleviates one or more symptoms of a movement disorder.

The compounds of the invention may also be useful as anxiety-reducing (anxiolytic) agents.

By "neurological disorder or disease" is meant a disorder or disease of the nervous system including, but not limited to, epilepsy, anxiety, multiple sclerosis, storkes, head trauma, spinal cord injuries, and chronic neurodegeneative diseases such as Parkinson's and Huntington's diseases, Alzheimer's disease, and amyotrophic lateral sclerosis. Also meant by "neurological disorder or disease" are those disease states and conditions in which an antispastic or anticonvulsant may be indicated, useful, recommended and/or prescribed.

By "neurodegenerative disease" is meant diseases such as, but not limited to, Huntington's Disease, Parkinson's Disease, Alzheimers Disease, and amyotrophic lateral sclerosis (ALS).

By "anticonvulsant" is meant a compound capable of reducing the severity, number, or duration of convulsions produced, observed, or found in conditions such as generalized tonic-clonic seizures, absence seizures, myoclonic seizures, simple partial seizures, complex partial seizures, secondarily generalized partial seizures, status epilepticus, and trauma-induced seizures as occur following head injury or surgery.

By "anticonvulsant activity" is meant efficacy in reducing the severity, number, or duration of convulsions produced, observed, or found in conditions such as generalized tonic-clonic seizures, absence seizures, myoclonic seizures, simple partial seizures, complex partial seizures, secondarily generalized partial seizures, status epilepticus, and trauma-induced seizures, as occur following head injury or surgey.

By "therapeutic dose" is meant an amount of a compound that relieves to some extent one or more symptoms of the disease or condition of the patient. Additionally, by "therapeutic dose" is meant an amount that returns to normal, either partially or completely, physiological or biochemical parameters associated with or causative of the disease or condition. Generally, it is an amount between about 0.1–15–20–30 mg/kg body weight, depending on the age, size, and disease associated with the patient. The dosing can be one to four times a day.

By "pharmaceutical composition" is meant a therapeutically effective amount of a compound of the present invention in a pharmaceutically acceptable carrier, i.e., a formulation to which the compound can be added to dissolve or otherwise facilitate administration of the compound. Examples of pharmaceutically acceptable carriers include water, saline, and physiologically buffered saline. Such a pharmaceutical composition is provided in a suitable dose. Such compositions are generally those which are approved for use in treatment of a specific disorder by the FDA or its equivalent in non-U.S. countries.

By "patient" is meant any animal that presents a symptom that can be alleviated by the administration of an anticonvulsant or antispastic composition. Preferably, the animal is a mammal. Most preferably, the animal is a human.

By "alkyl" is meant a branched or unbranched hydrocarbon chain containing between 1 and 6, preferably between 1 and 4, carbon atoms, such as, e.g., methyl, ethyl, n-propyl, iso-propyl, n-butyl, sec-butyl, iso-butyl, tert-butyl, 2-methylpentyl, cyclopropylmethyl, allyl, and cyclobutylmethyl.

By "lower alkyl" is meant a branched or unbranched hydrocarbon chain containing between 1 and 4 carbon atoms, of which examples are listed herein.

By "hydroxyalkyl" is meant an alkyl group as defined above, substituted with a hydroxyl group.

3. METHODS FOR PREPARING PHARMACEUTICAL FORMULATIONS AND COMPOSITIONS

As demonstrated herein, useful compounds of this invention and their pharmaceutical compositions may be used to treat neurological disorders or diseases. While these compounds will typically be used in therapy for human patients, they may also be used to treat similar or identical diseases in other vertebrates such as other primates, domestic animals, farm animals such as swine, cattle, and poultry, and sports animals and pets such as horses, dogs, and cats.

The pharmaceutical formulations and compositions of the present invention can be prepared according to known methods to prepare pharmaceutically useful compositions, whereby active agents are combined in a mixture with a pharmaceutically acceptable carrier. For instance, see Gennaro (Ed.), REMINGTON'S PHARMACEUTICAL SCIENCES, 18th ed. (Mack Publishing Co. 1990) and GOODMAN AND GILMAN'S, cited above. A composition is said to be in a "pharmaceutically acceptable carrier" if its administration can be tolerated by a recipient patient. Sterile phosphate-buffered saline is one example of a pharmaceutically acceptable carrier. Other suitable carriers (e.g., saline and Ringer's solutions) are well known to those skilled in the art. See, for example, REMINGTON'S PHARMACEUTICAL SCIENCES, supra.

Pharmaceutically acceptable salts are generally well known to those of ordinary skill in the art, and may include, by way of example but not limitation, acetate, benzenesulfonate, besylate, benzoate, bicarbonate, bitartrate, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/disphosphate, polygalacturonate, salicylate, stearate, subacetate, succinate, sulfate, tannate, tartrate, or teoclate. other pharmaceutically acceptable salts may be found in, for example, *Remington's Pharmaceutical Sciences,* Mack Publishing Co., Easton, Pa. (18th ed. 1990).

Preferred pharmaceutically acceptable salts include, for example, acetate, benzoate, bromide, carbonate, citrate, gluconate, hydrobromide, hydrochloride, maleate, mesylate, napsylate pamoate (embonate), phosphate, salicylate, succinate, sulfate, or tartrate.

The useful compounds of this invention may also be in the form of pharmaceutically acceptable complexes. Pharmaceutically acceptable complexes are known to those of ordinary skill in the art and include, by way of example but not limitation, 8-chlorotheophyllinate (teoclate).

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

In general, the dosages of the anticonvulsant and antispasticity agents described herein will vary depending upon such factors as the patient's age, weight, height, sex, general medial condition, and previous medical history. For purposes of therapy, a compound of the present invention and a pharmaceutically acceptable carrier are administered to a subject in need of such treatment in a therapeutically effective amount. The combination of active agent and carrier is said to be administered in a "therapeutically effective amount" if the amount administered is physiologically significant. An agent is physiologically significant if its presence results in a detectable change in the physiology of a recipient patient. In the present context, for example, the anticonvulsant agent is physiologically significant if the presence of the agent results in the reduction of the severity, number or duration of convulsions, while an antispasticity agent is physiologically significant if the presence of the agent results in the alleviation of one or more symptoms of spasticity.

The compositions and formulations of the present invention can be administered orally using solid oral dosage forms such as, for example, enteric-coated tablets, caplets, gelcaps, sprinkles, or capsules, or via liquid oral dosage forms such as syrups or elixirs. The indicated dosage of 3,3-bis(3-fluorphenyl)propanamide and structurally related bis (fluorophenyl)alkylamide compounds as anticonvulsants is on the order of 1–1000 mg per dose, and preferably 10–500 mg per dose. Unit solid oral dosage forms preferably contain about 10–250 mg per tablet or capsule, which should preferably be taken 1–2 at a time for a maximum of two times per day, at a dosage of about 01.–15 mg/kg body weight. Liquid formulations can also be employed with active ingredient compositions so as to provide 1–2 teaspoonfuls per dose. Furthermore, corresponding reduced dosage pediatric chewable and liquid oral dosage forms can also be administered. These compounds also can be added to foods and beverages in the form of drops (with a dropper from a "concentrate" preparation) for oral administration. In addition, the compounds of the invention may be formulated into chewing gum to facilitate oral delivery and absorption.

Alternatively, the compounds of the invention can be administered by injection or other systemic routes, such as transdermal or transmucosal administration, for example, nasally, buccally, or rectally, via suppositories or using sublingual, vaginal, or intestinal administration; parenteral delivery, including intramuscular, subcutaneous, and/or intramedullary injections, as well as intrathecal, direct intraventricular, intravenous, intraperitoneal, intranasal, or intraocular injections. Oral administration is much more convenient, however, and therefore is preferred.

For use in an oral antispasticity formation or composition, the dosage level of active ingredient(s) is on the order of 1–1000 mg per dose, and preferably, 10–250 mg per dose, or 0.1–1.5 mg/kg body weight. The exact formulation, route of administration and dosage can be chosen by the individual physician in view of the patient's condition. (See e.g. Fingl et al., in *The Pharmacological Basis of Therapeutics*, 1975, Ch. 1, p. 1).

It should be noted that the attending physician would know how and when to terminate, interrupt, or adjust administration due to toxicity or organ dysfunction. Conversely, the attending physician would also know to adjust treatment to higher levels if the clinical responses were not adequate (precluding toxicity). The magnitude of an administered dose in the management of the disorder of interest will vary with the severity of the condition to be treated and to the route of administration. The severity of the condition may, for example, be evaluated in part, by standard prognostic evaluation methods. Further, the dose and perhaps dose frequency, will also vary according to the age, body weight, and response of the individual patient. A program comparable to that discussed above may be used in veterinary medicine.

For injection, the agents of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to a use in humans, the compounds of the invention can be used in veterinary applications, for example, as anticonvulsant agents, anxiolytic agents, or antispasticity agents, in animals such as cats, dogs, birds, horses, cattle, mink, poultry, and fish. In such cases, the active compound(s) may be administered by injection or other systemic routes, such as transdermal or transmucosal administration (for example, rectal administration via suppositories), or orally by addition to food or drink. As an anticonvulsant agent, the indicated oral dosage of the compounds of the invention per kilogram or body weight of such animals is about 1–1000 mg/kg, depending upon the species of animal and the route of administration. A preferred range for oral dosage is about 10–500 mg/kg body weight.

The indicated oral dosage of the compounds of the invention per kilogram body weight as antispasticity agents for animals is in the range of about 1–1000 mg/kg, depending upon the species of animal and the route of administration. A preferred range for oral dosage is about 5–500 mg/kg body weight.

The present invention thus contemplates a variety of pharmaceutical compositions the compounds of the invention as active ingredients that are suitable for oral, parenteral, transdermal, transmucosal, intranasal, buccal, or rectal administration.

It is further understood that the compounds of the invention can be used in combination with other pharmaceutically active ingredients.

4. DEMONSTRATING THERAPY-IMPLICATING ACTIVITY

The suitability and effectiveness of a given compound, pharmaceutical formulation, or composition for the alleviation of a pathology, as discussed above, can be demonstrated using appropriate animal models such as (but not limited to) those described below.

(a) Anticonvulsant Activity

Methods for determining and evaluating the in vivo anticonvulsant activity of test compounds in experimental animals (e.g., rodents) are well known in the art (Foye, W. O. (Ed.), Principles of Medicinal Chemistry, 3rd ed. (1989) Lea and Febiger, Philadelphia, Pa. pp. 173–178; Gilman, A. G., et al., Goodman and Gilman's The Pharmacological Basis of Therapeutics, 9th ed. (1996) Pergamon Press, New York, pp. 461–486; Wolff, M. E., Burger's Medicinal Chemistry, 5th ed. (1996), Wiley-Interscience, New York, pp. 182–198. Relevant animal models include the Frings audiogenic seizure-susceptible mouse and the rat MES (Maximal Electroshock) assays. Both of these assays were used to assess the anticonvulsant properties of the test compounds. For general methods and terminology relating to anticonvulsant assays, see J. A. Vida, "Anticonvulsants," in W. O. Foye et al. (Eds.), Principles of Medical Chemistry, $4^{th}$ Ed. (1995) pp. 182–198.

There are numerous in vivo models involving different kinds of seizures and behavioral effects that are relevant for clinically distinct forms of epilepsy. It therefore is useful to test for effects in more than one model.

Loscher and Schmidt (Epilepsy Research 17:95–134, 1994) proposed a test hierarchy in various animal models of epilepsy for the pharmacologic evaluation of antiepileptic drugs. A more detailed description of these various models as well as the possible correlates to human epilepsy can be found in reviews by H. S. White (in Antiepileptic Drugs, Fourth Edition, edited by R. H. Levy, R. H. Mattson, and B. S. Meldrum, Raven Press, Ltd., New York, 1995, pp 99–110) and H. Kupferberg (Epilepsia 30 (Suppl 1): S51–S56, 1989).

One useful model is provided by the Frings audiogenic seizure-susceptible mouse, a model of reflex epilepsy. The Frings audiogenic seizure-susceptible mouse is a genetic mouse model of epilepsy used to indicate a preliminary, general level of efficacy and therapeutic potential, but is not predictive of any particular human seizure disorder. Compounds are measured for their ability to block sound-induced tonic extension seizures (White et al., 1995). At the time of testing, individual mice are placed into a round Plexiglas chamber and exposed to a sound stimulus of 110 decibels, 11 kHz, for 20 seconds. Animals not displaying tonic hindlimb extensions are considered protected. In addition, the seizure score for each mouse can be recorded as: (1) running for less than 10 seconds; (2) running for greater than 10 seconds; (3) clonic activity of limbs and/or vibrissae, (4) forelimb extension/hindlimb flexion; and (5) hindlimb extension.

The average seizure score can be calculated for each group of mice employed in the dose-response study. At each dose, mice are also tested on a rotarod for testing of motor impairment ("toxicity"). Testing for motor impairment on the rotarod involves placing a mouse for a three-minute period on a one-inch diameter rod and rotating at six revolutions per minute. If the mouse falls off of the rotating rod three times within the three-minute period, it is considered a toxic response.

b) The Maximal Electroshock Seizure (MES) Test

The Maximal Electroshock Seizure (MES) Test is a highly predictive animal seizure model of human generalized tonic-clonic seizures. In the MES test, a 60-Hz alternating current is delivered for 0.2 sec through corneal electrodes in mice. Abolution of the hind-limb tonic extensor component is taken as the endpoint for this test. Absence of this component suggests that the test substance has the ability to prevent the spread of seizure discharge through neural tissue (White et al., 1995)

c) The Acute/Chronic Spinally Transected Rat and the Acute Decerebrate Rat

There are several models of spasticity, including the acute decerebrate rat, the acute or chronic spinally transected rat, and the chronically spinal cord-lesioned rat. (see, e.g., Bertman and Adkovat, Brain Res. 684:8–18 (1995); Chen et al., Neuroscience 23:641–647 (1987)). The acute models, although of proven value in elucidating the mechanisms involved in the development of spasticity, have come under criticism due to the fact that they are acute.

The animals usually die or have total recovery from spasticity. The spasticity develops immediately upon intervention, unlike the spasticity that evolves in the human condition of spasticity, which most often initially manifests itself as a flaccid paralysis. Only after weeks and months does spasticity develop in humans. Some of the more chronic-lesioned or spinally transected models of spasticity do post-operatively show flaccid paralysis. At approximately four weeks post-lesion/transection, the flaccidity changes to spasticity of variable severity.

Although all of these models have their own particular disadvantages and lack of true representation of the human spastic condition, they have provided much information about the nature of spasticity. These models have also provided methods to test various treatment paradigms that have led to similar treatments being tested in humans. Many of these models have also made use of different species, such as cats, dogs, and primates.

Baclofen, diazepam (Valium), and tizanidine are effective on different parameters of spasticity (EMG recordings, H-reflex, the H/M ratio, mono- and polysynaptic reflexes, clonus, hyperreflexia) in these models. The flexor reflex is a polysynaptic response elicited by stimulation of the bottom of the foot and models the withdrawal reflex. Compounds such as baclofen, the benzodiazepines, tizanidine, and NMDA receptor antagonists have been shown to reduce the flexor reflex in rodents (normal or spinally transected) and are also effective antispastics in humans (Bertman and Advokat, 1995; Hao, 1990; Young, 1994; Davidoff, 1985).

(d) Primary Observation Irwin Test in the Rat

This method is based on that described by Irwin, Psychopharmacologia 13: 222–257 (1968). It is used to detect physiological, behavioral, and toxic effects of a test substance, and indicates a range of dosages that can be used for later experiments. Typically, rats (three per group) are administered the test substance and are then observed in comparison with a control group given vehicle. Behavioral modifications, symptoms of neurotoxicity, pupil diameter, and rectal temperature are recorded according to a standardized observation grid derived from that of Irwin. The grid contains the following items: mortality, sedation, excitation, aggressiveness, Straub tail, writhes, convulsions, tremor, exophthalmos, salivation, lacrimation, piloerection, defecation, fear, traction, reactivity to touch, loss of righting reflexes, sleep, motor incoordination, muscle tone, stereotypies, head-weaving, catalepsy, grasping, ptosis, respiration, corneal reflex, analgesia, abnormal gait, forepaw treading, loss of balance, head twitches, rectal temperature, and pupil diameter. Observations are performed at 15, 30, 60, 120, and 180 minutes following administration of the test substance, and also 24 hours later.

(e) Rotarod Test in the Rat and Mouse

This is a test of neurological deficits using the method described by Dunham et al., J. Am. Pharm. Assoc. 46: 208–209 (1957). Rats or mice are placed on a rod rotating at a speed of six to eight turns per minute. The number of animals which drop off of the rod before three minutes is counted and the drop-off times are recorded (maximum: 180 sec). Eight to ten rats are studied per group and the test is performed blind. The test compound is administered i.p. 60 min prior to testing. Diazepam (Valium), a benzodiazepine, is administered at 8 mg/kg, i.p., as the reference substance. A control group administered the vehicle is also included in the study.

(f) Anti-Manic Activity

To assess the possible use of compounds in the treatment of affective mood disorders, such as bipolar mood disorder, one can employ the amphetamine-induced hyperactivity model in rats. In addition to being a test for classical and atypical antipsychotic activity, this procedure has also been proposed as a simple animal model of manic behavior. Costall et al., *Brain Res.* 123: 89–111 (1977).

(g) Neurogenic Inflammation of the Meninges

Neurogenic inflammation within the meninges has been proposed as an event in the underlying pathology of migraine headaches. Lee et al., *Brit J. Pharmacol.* 116: 1661–1667 (1995). Compounds are tested for their ability to block the leakage of radiolabeled bovine serum albumin within the dura mater post trigeminal stimulation.

(h) Analgesic Properties

There are many whole-animal assays for determining analgesic properties, such as writhing, hot-plate, tail-flick, arthritic pain, paw pressure tests, and the Bennet or Chung models of neuropathic pain. Albe-Fessard et al., in ADVANCES IN PAIN RESEARCH AND THERAPY 13, pages 11–27 (Raven Press 1990).

(i) Therapeutic Benefit Relative to Movement Disorders and Restlessness Syndromes Animal models exist for the study of movement disorders and restlessness syndromes, for example, drug-induced akathisias, serotonin syndrome, and rotation induced by unilateral nigral lesions. Lloyd and Morselli (1987), supra. Additionally, individual case reports of anecdotal efficacy of compounds in humans have been a source for support for these indications. Mellick and Mellick (1995), supra; Olson et al., *Am. J. Med.* 102: 60–66 (1997).

Anxiolytic activity of the compounds of the invention can be demonstrated using appropriate methods known in the art, such as those described in Balandrin et al., U.S. Pat. No. 5,506,268 (1996).

The therapeutic effects of the compounds of the invention in various of the assays described above, combined with a general lack of toxicity, make the compounds of the present invention ideal agents for the treatment of the pathologies described above, including convulsions/seizures (epilepsy) and spasticity. With this background, the present invention will be understood more readily by reference to the following examples, which are provided for purposes of illustration and are not intended to be limiting of the invention.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the claims below.

All publications mentioned in this specification are indicative of the level of skill of those in the art to which the invention pertains. All publications are herein incorporated by reference to the same extent as if each individual publication were specifically and individually indicated to be incorporated by reference in its entirety.

EXAMPLES

Example 1

Anticonvulsant Activity

Desired properties of an anticonvulsant drug include: the drug can be administered by oral or injectable routes, the drug exhibits effective anticonvulsant activity against several seizure types, including, but not limited to, generalized tonic-clonic seizures, absence seizures, myoclonic seizures, simple partial seizures, complex partial seizures, secondarily generalized partial seizures, status epilepticus, and trauma-induced seizures, as occur following head injury or surgery; and the drug is devoid of or has minimal side effects such as impairment of cognition, disruption of motor performance, sedation or hyperexcitability.

Example 2

Synthesis of Compounds

Capillary gas chromatographic and low-resolution mass spectral data were obtained using a Hewlett-Packard (HP) 5890 Series II Gas Chromatograph coupled to an HP 5971 Series Mass Selective Detector [Ultra-2 Ultra Performance Capillary Column (cross-linked 5% PhMe silicone); column length, 25 m; column i.d., 0.20 mm; Helium flow rate, 60 mL/min; injector temp., 250° C.; temperature program, 20° C./min from 125 to 325° C. for 10 min, then held constant at 325° C. for 6 min].

Thin-layer chromatography was performed using Analtech Uniplate 250-µm silica gel HF TLC plates. UV light in conjunction with ninhydrin and Dragendorff's spray reagents (Sigma Chemical Co.) were used for detecting compounds on the TLC plates. Most reagents used in reactions were purchased from the Aldrich Chemical Co. (Milwaukee, Wis.), Sigma Chemical Co. (Saint Louis, Mo.), Fluka Chemical Corp. (Milwaukee, Wis.), Fisher Scientific (Pittsburgh, Pa.), TCI America (Portland, Oreg.), or Lancaster Synthesis (Windham, N.H.).

Preparation of 4,4-bis(4-fluorophenyl)butanamide (Compound 12)

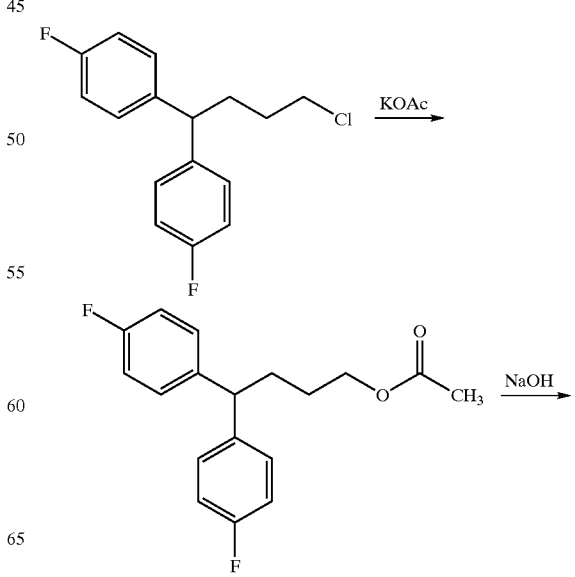

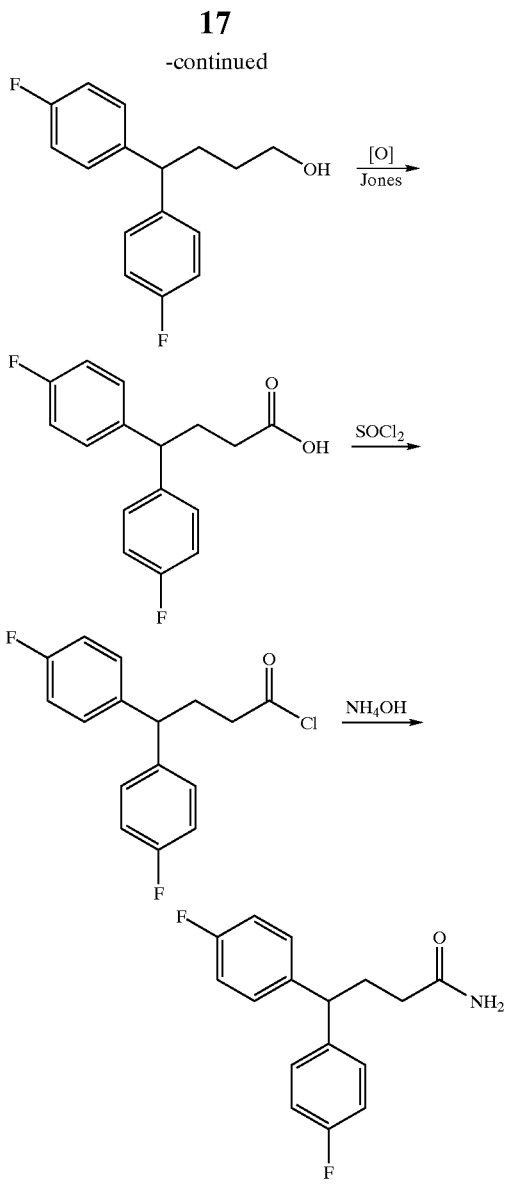

(a) Preparation of 1-acetoxy-4,4-bis(3-fluorophenyl) butane

A solution of chloride (20.0 g, 71.2 mmol) in DMF (50 mL) and potassium acetate (14.0 mg, 142 mmol) was heated to 140° C. for 60 min (start time 12:36 min). Cooled to 25° C., poured into 200 mL sat. NaCl, and extracted product with EtOAc (2×100 mL), washed EtOAc layer with sat. NaCl (3×100 mL), dried ($Na_2SO_4$), and evaporated under vacuum to provide 19.43 g, 89.8% yield of an orange oil.

(b) Preparation of 4,4-bis(3-fluorophenyl)-1-butanol

A solution of the ester (19.4 g, 63.9 mmol) in abs. EtOH (250 mL) and 10N NaOH (6.4 mL, 64 mmol) was heated to reflux for 60 min. The solvent was then evaporated under vacuum. The residue was dissolved in EtOAc (200 mL), sat. NaCl (100 mL), and $H_2O$ (10 mL). The layers were separated and the organic layer was washed with sat. NaCl (3×50 mL), dried (anhyd. $Na_2SO_4$), and evaporated under vacuum to provide 15.4 g, 92.2% yield of an oil. TLC (Hex/EtoAc, 3:1), Rf=0.23.

(c) Preparation of 4,4-bis(3-fluorophenyl)butyric acid

Chromium trioxide (27.9 g, 279 mmol) was dissolved in $H_2O$ (42 mL) and was cooled in an ice bath. Conc. $H_2SO_4$ (24 mL) was added with shaking. This suspension was added dropwise to a solution of the alcohol (15.4 g, 55.8 mmol) in acetone over 10 min. Stirred vigorously for 15 min then $H_2O$ (200 mL) was added and the product was extracted with EtOAc (2×100 mL). The organic layer was washed with $H_2O$ (2×50 mL), dried ($Na_2SO_4$), and evaporated under vacuum to provide 14.0 g, 90.7% of a greenish glass. This material was chromatographed on silica gel (50×300 mm) elution with $CHCl_3$ (1 L), 3% MeOH/$CHCl_3$ (0.5 L), then Hex/EtOAc [1:1] (1 L) to provide 10.3 g, 67.1% of carboxylic acid as a viscous oil: GC/MS: Rt=7.56 min, m/z 276.

(d) Preparation of 4,4-bis(3-fluorophenyl)butyrylchloride

A mixture of the carboxylic acid (10.3 g, 37.5 mmol) and thionyl chloride (8.20 mL, 112 mmol) was heated to 85° C. in an oil bath with vigorous stirring for 6 h. The solution was then cooled to room temperature and excess thionyl chloride was removed by rotary evaporation (1 h, 1 mm Hg, 100° C.) and the residual thionyl chloride was azeotroped with benzene (2×100 mL). This procedure povided the acid chloride as a liquid, 10.5 g, 95.1%.

(e) Preparation of 4,4-bis(3-fluorophenyl)butanamide

A solution of the acid chloride (1.75 g, 5.94 mmol) in EtOAc (50 mL) was added dropwise over a period of 15 min to a vigorously stirring solution of conc. aq. $NH_4OH$ (2.1 mL, 17.8 mmol, 3 equivt) in $H_2O$ (50 mL). The biphasic mixture was then stirred for 1 h at room temperature. The organic layer was separated and washed with 1 M HCl (3×25 mL), 1 M NaOH (2×30 mL), and sat. aq. NaCl (2×25 mL). The organic layer was then filtered, dried (anhyd. $Na_2SO_4$), filtered again, and the solvent was removed under vacuum to provide crude product as an oil which crystallized on standing. This material was chromatographed on silica gel, elution with hex/EtOAc [1:1] followed by 5% MeOH/$CHCl_3$; fractions containing product where pooled and evaporated under vacuum to provide 1.13 g, 72.3% yield of amide as a colorless oil which crystallized on standing. TLC Hex/EtOAc [1:1], Rf 0.23; GC/EIMS, Rt=64 min m/z 263.

Preparation of 4,4-bis(3-fluorophenyl)butanamide (Compound 11)

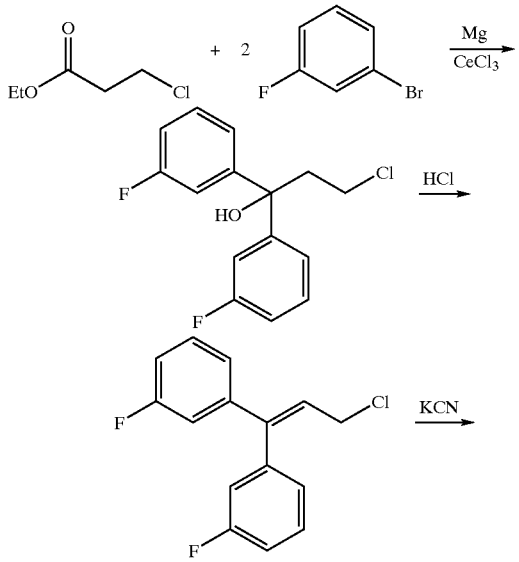

-continued

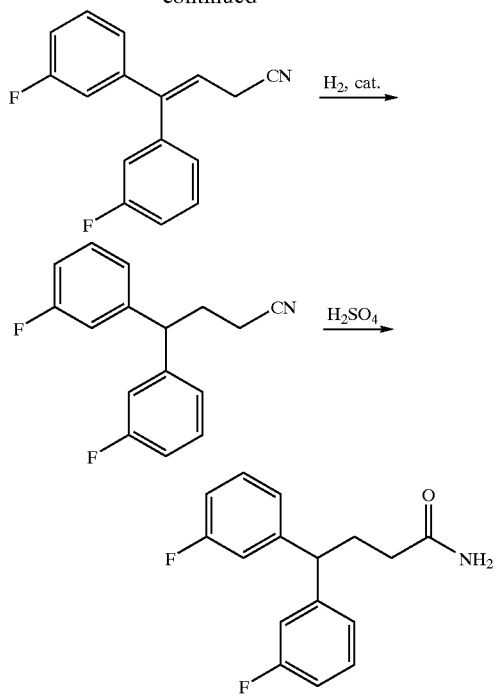

(a) Preparation of 3,3-bis(3-fluorophenyl)-3-hydroxypropylchloride

Cerium chloride heptahydrate (81.8 g, 220 mmol, 3.0 equivt) was finely ground in a mortar then placed in a 1-L flask and was heated in a vacuum oven at 130° C. and 0.1 mm Hg for 18 h. The anhydrous cerium chloride was then suspended in THF (400 mL). Ethyl 3-chloropropionate (10.0 g, 73.2 mmol) was then added and the reaction mixture was stirred at room temperature for 1 h. The mixture was then cooled in an ice bath and stirred for 30 min at 0° C.

Meanwhile, the Grignard reagent was prepared as follows. In a 500 mL, 3-necked flask, to a suspension of Mg (5.34 g, 220 mmol) in THF (320 mL) was added 1/20 of bromofluorobenzene (39.7 g, 227 mmol) with $I_2$ (1 crystal). The reaction mixture was heated to reflux. After initiation, the rest of the bromide was added dropwise over a period of 10 min. The reaction was then refluxed for 30 min. The solution was cooled to 0° C. in an ice bath and transferred via canula to the mixture of cerium chloride and ester in THF over a period of 20 min. The reaction was stirred for 1 h at 0° C., then 1 h at room temperature. After 1 h at room temperature, it was cooled in an ice bath, 10% aq. HCl (250 mL) was added, and the layers separated. The lower aqueous layer was washed with $CHCl_3$ (2×100 mL). The organic layers were combined and evaporated under vacuum to yield 22.3 g, 108% of a green-brown oil.

(b) Preparation of 3,3-bis3-fluorophenyl)2-propenylchloride

A solution of 22.3 g, 78.9 mmol of tertiary alcohol was stirred at 100° C. with conc. HCl (200 mL) for 1 h. The reaction was then cooled and diluted with $H_2O$ (300 mL). The mixture was extracted with $CHCl_3$ (4×50 mL) and evaporated under vacuum to provide crude product. This material was chromatographed on a 50×300 mm silica column (elution with Hex/EtOAc (30:1), then [20:1]). Fractions containing product were combined and evaporated to provide 11.4 g (54% yield) of product as a colorless oil.

(c) Preparation of 4,4-bis(3-fluorophenyl)-3-butenenitrile 6.94 g, 26.2 mmol of chloride was dissolved in EtOH (100 mL). KCN (17.1 g, 262 mmol, powdered) was added and the reaction mixture was refluxed. After 3 h, the volatiles were evaporated under vacuum. The residue was dissolved in diethyl ether (100 mL), washed with $H_2O$ (3×25 mL), dried (anhyd. $Na_2SO_4$), and evaporated to provide the crude product. Chromatography on silica gel (50×300 mm) Hex/EtOAc [10:1] provided 5.05 g, 75.6% yield of a yellow oil. TLC (Hex/EtOAc, [10:1]) Rf=0.32.

(d) Preparation of 4,4-bis(3-fluorophenyl)-3-butylnitrile 5.05 g, 19.8 mmol of alkene was dissolved in EtOH (100 mL). 10% Pd/C was added and the mixture was hydrogenated on a Parr apparatus at 25° C., 60 psig. After shaking for 0.5 h, the mixture was filtered through Celite and the filtrate was evaporated under vacuum to yield 4.5 g (88.4%) of a colorless oil.

(e) Preparation of 4,4-bis(3-fluorophenyl)butanamide

The nitrile (4.50 g, 17.5 mmol) was dissolved into conc. $H_2SO_4$ (10 mL). The reaction solution was then stirred for 30 min at room temperature. The reaction was then heated to 50° C. in an oil bath. After 1.75 h at 50° C., the reaction solution was poured onto a mixture of ice/water (100 mL). The solution was extracted with hot EtOAc (8×100 mL), dried ($Na_2SO_4$), and evaporated under vacuum to provide crude product as a thick oil. This material was chromatographed on silica gel (50×300 mm, elution with 5% MeOH/$CHCl_3$) and rechromatographed with 3% MeOH/$CHCl_3$. Evaporation of the fraction containing product provided 0.771 g, 16.0% of a white powder.

Synthesis of 3,3-bis(3-fluorophenyl)propanamide (Compound 1)

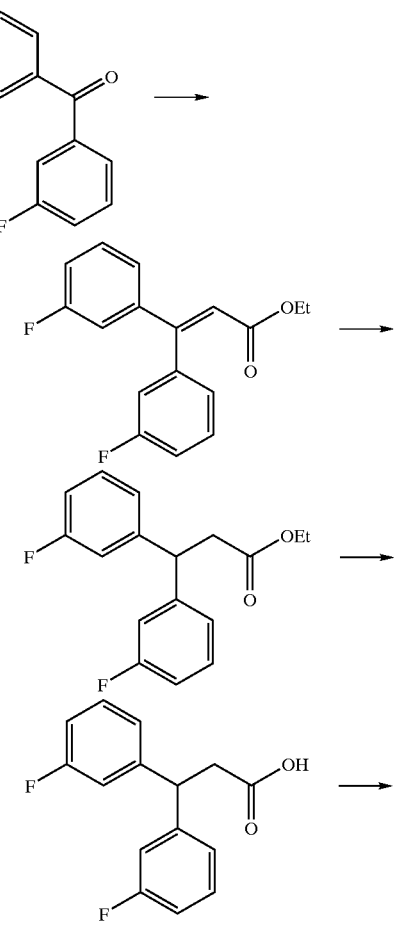

-continued

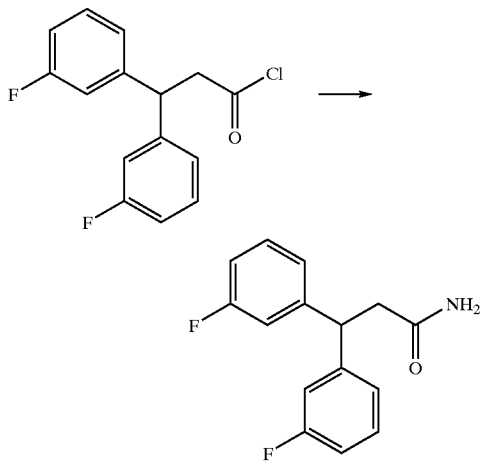

(a) Preparation of ethyl 3,3-bis(3-fluorophenyl)acrylate

A suspension (under argon) of sodium hydride (3.63 g, 151.2 mmol) in dimethylformamide (DMF, 500 mL) was treated dropwise with a solution of triethyl phosphonoacetate (37.0 g, 165.0 mmol) in DMF (200 mL). The reaction was heated at 65EC for 2 hr. After this time the reaction was cooled to 0° C. and treated with a solution of 3.3'-difluorobenzophenone (30.0 g, 137.5 mmol) in DMF (200 mL).

The reaction was stirred at ambient temperature for 16 hr. The reaction was quenched by the addition of water (1 L) and equilibrated with hexane-ethyl acetate (1:1, 2 L). The aqueous phase was separated and washed one additional time with hexane-ethyl acetate (1:1, 2 L). The organic phases were combined, washed with brine, dried over anhydrous $MgSO_4$, filtered, and concentrated to afford 38.81 g (98%) of the title compound as a clear, colorless oil. GC/EI-MS analysis gave a single component (Rt=6.38 min, m/z (rel.int.) 288 (M+,11), 259 (8), 243 (54), 214 (100), 194 (53), 175 (30), 123 (38), 120 (48), 94 (38), and 75 (74).

(b) Preparation of ethyl 3,3-bis(3-fluorophenyl) propionate

A solution of ethyl 3,3-bis(3-fluorophenyl)acrylate (38.81 g, 134.8 mmol) in absolute ethanol (300 mL) was hydrogenated in the presence of palladium hydroxide on carbon (5 g wet, Degussa type) at 60 p.s.i. $H_2$ for 30 min at ambient temperature. After this time the reaction was filtered and concentrated to afford 39.08 g (100%) of the title compound as a clear, colorless oil. GC/EI-MS analysis gave a single component: Rt=6.21 min, m/z (rel.int.) 290 (M+,6), 262 (1), 244 (5), 216 (100), 203 (67), 201 (48), 183 (63), 101 (41), 96 (17), and 75 (25).

(c) Preparation of 3,3-bis(3-fluorophenyl)propionic acid

A solution of ethyl 3,3-bis(3-fluorophenyl)propionate (39.08 g, 134.8 mmol) in absolute ethanol (500 mL) was treated with 5N NaOH (500 mL) and stirred at ambient temperature for 16 hr. After this time the reaction mixture was concentrated (removal of ethanol) on a rotary evaporator and diluted with water (1 L). The aqueous mixture was washed once with diethyl ether (500 mL) and the remaining aqueous mixture acidified (pH~1) by the addition of concentrated HCl. The aqueous phase was extracted with methylene chloride (4×250 mL). The combined organic extracts were dried over anhydrous $MgSO_4$, filtered, and concentrated to afford 31.76 g (90%) of the title compound as a white solid. GC/EI-MS analysis gave a single component: Rt=6.60 min, m/z (rel. int.) 262 (M+, 13), 243 (1), 216 (40), 203 (85), 201 (54), 183 (100), 170 (11), 121 (31), 101 (43), 96 (24), and 75 (45).

(d) Preparation of 3,3-bis(3-fluorophenyl)propanamide 3,3-bis(3-fluorophenyl)propionic acid (31.31 g, 119.5 mmol) was dissolved in thionyl chloride (100 mL) and heated at reflux for 16 hr. After this time the excess thionyl chloride was removed by distillation and the remaining oil, the acid chloride product, dissolved in dichloromethane (200 mL). The solution of acid chloride was added dropwise to a stirred solution (−78° C.) of ammonia (35 mL) in dichloromethane (500 mL), followed by the addition of pyridine (100 mL). The reaction was stirred at rt for 1 h and quenched with 10% HCl (500 mL). After equilibration, the aqueous phase was removed and the remaining organic phase was washed with 10% HCl (3×500 mL). The organic phase was dried over anhydrous $MgSO_4$, filtered, and concentrated to a solid. The solid was dissolved in diethyl ether (1 L) and washed with 1N NaOH (4×500 mL), 10% HCl (3×500 mL), and brine (500 mL). The organic solution was dried over anhydrous $MgSO_4$, filtered, and concentrated to a solid (28.24 g). Recrystallization of this material from hot toluene (100 mL, washing with 100 mL of 0° C. toluene) gave 25.39 g (81%) of the title compound as a white, crystalline solid: m.p. 103–105° C.; GC/EI-MS analysis gave a single component at Rt=7.43 min, m/z (rel. int.) 261 (M+, 15), 244 (2), 216 (27), 203 (25), 201 (41), 183 (57), 170 (7), 164 (9), 149 (8), 133 (6), 121 (52), 111 (15), 109 (20), 101 (41), 96 (27), 95 (24), 75 (42), and 44 (100).

Synthesis of N-tert-butyl-3,3-bis(3-fluorophenyl) propanamide (Compound 5)

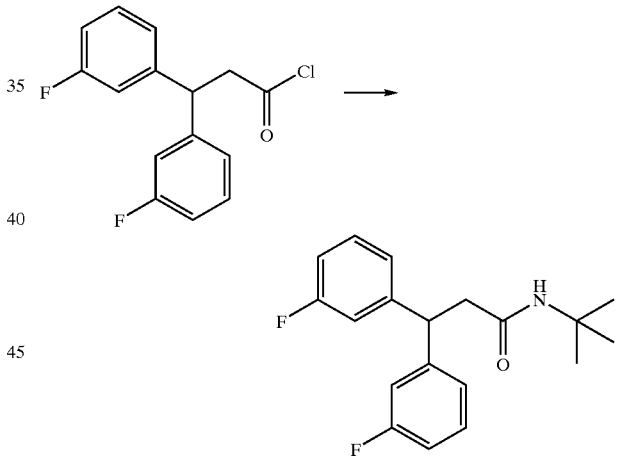

To a −78° C. solution of the acid chloride (5 g, 17.8 mmol [15.5 mmol actual]) in $CH_2Cl_2$ (50 mL) was added in a stream t-butyl amine (5.6 mL, 3.91 g, 53.5 mmol, 3 equivt). The dry-ice bath was removed and the reaction mixture was then stirred for 4 h at room temperature. The mixture was then poured into diethyl ether (100 mL) and the organic layer was washed with 1 M HCl (4×50 mL), 1 M NaOH (3×50 mL), and $H_2O$ (3×50 mL). The organic layer was then filtered (paper), dried (anhydr. $Na_2SO_4$), filtered again, and the solvent was removed under vacuum to provide 4.34 g, 93% of product as a cream-colored powder. TLC analysis: Hex/EtOAc [3:1], showed one major spot. This material was recrystallized from abs. EtOH/$H_2O$ [1:1] (100 mL) plus abs. EtOH (10 mL, to dissolve) to provide 3.59 g, 76.7% yield of product as light-straw-colored needles. TLC Hex/EtOAc [1:1], Rf=0.76; GC/EIMS, Rt=7.55 min, m/z=317.

Synthesis of 3,3-bis(4-fluorophenyl)propanamide (Compound 10)

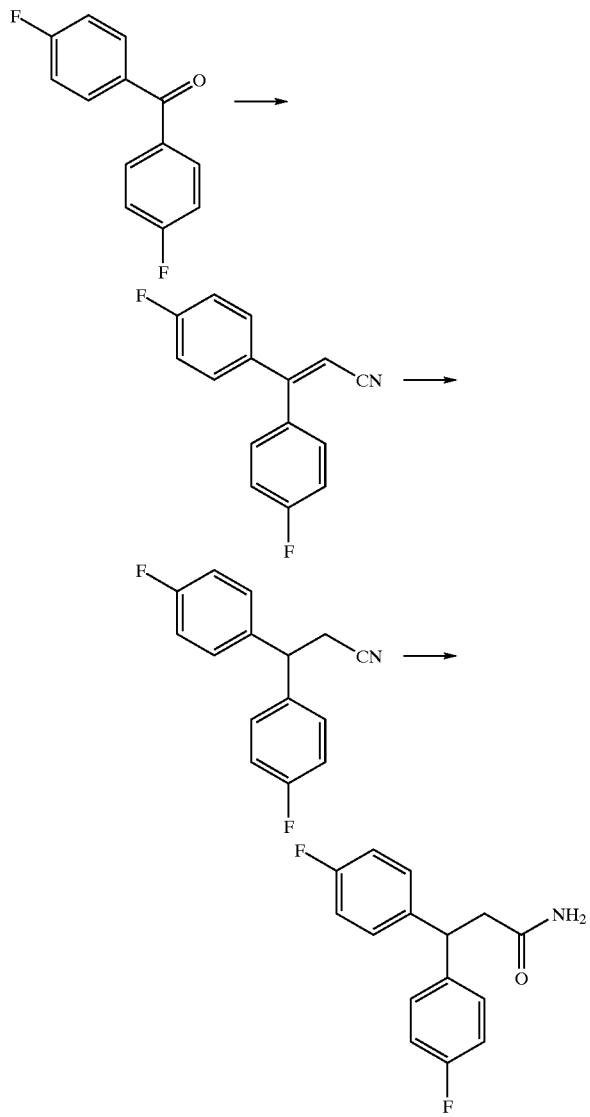

(a) Preparation of 3,3-bis(4-fluorophenyl)acrylonitrile

Using a nitrogen atmosphere, to a solution of diethyl cyanomethylphosphonate (8.52 g, 48.1 mmol) dissolved in DMF (100 mL) was added NaH (2.02 g, 50.4 mmol, 60% dispersion in mineral oil) in portions over a period of 5 min. The reaction was stirred at 25° C. for 15 min. Difluorobenzophenone (10 g, 45.8 mmol) then was added and the reaction was stirred 18 h at room temperature. The reaction mixture was then poured in $H_2O$ (400 mL) and extracted with $CHCl_3$ (7×100 mL). The combined organic layers were evaporated in vacuo and the residue was redissolved in diethyl ether (150 mL). The ether layer was washed with brine (3×100 mL), dried (anhyd. $Na_2SO_4$), and evaporated under vacuum to provide 9.53 g, 86.3% of crude point as a light-purple solid. GC/EIMS Rt=6.16 min m/z=241; TLC: Hex/EtOAc [10:1] Rf=0.34, major spot, >95%, light impurity at origin.

(b) Preparation of 3,3-bis(4-fluorophenyl)propionitrile

A solution of 9.53 g, 39.5 mmol of aklene-nitrile dissolved in EtOH (80 mL) was hydrogenated at 60 psig $H_2$ over 10% $Pd(OH)_2/C$ (20% Pd, Fluka, 1.90 g). After shaking for 8 h, the catalyst was removed by filtration through fritted glass. The solvent in the filtrate was evaporated under vacuum and the crude product was isolated as an oil. This material was chromatographed (50 mm×30 cm, elution with hexane/ethyl acetate [10:1] to [8:1]). Fractions containing product were combined and evaporated to provide 9.66 g, 100% of product as a yellow oil. GC/EIMS, Rt=7.18 min, m/z=243; TLC.

(c) Preparation of 3,3-bis(4-fluorophenyl)propanamide

The nitrile (9.66 g, 39.8 mmol) was dissolved into conc. $H_2SO_4$ (12 mL). The reaction solution was then stirred for 15 min at room temperature followed by 15 min at 50° C. Water (200 mL) was added to the cooled reaction mixture followed by ethyl acetate (100 mL). The layers were separated and the aqueous layer was extracted with EtOAc (100 mL). The combined organic layers were washed with $H_2O$ (2×50 mL), sat. aq. $NaHCO_3$ (50 mL), dried (anhydr. $Na_2SO_4$), and evaporated under vacuum to provide crude product. This material was chromatographed (50×300 mm, elution with ethyl acetate/hexane [1:3]). Fractions containing product were combined and evaporated to provide 2.34 g, 22.5% of product as a white solid. GC/MS, Rt=7.93 min m/z=261; TLC: Hex/EtOAc [1:1], Rf=0.20, single spot UV/Vis; $^1$H-NMR (d, J=8 Hz, 2H), 4.55 (t, J=8 Hz, 1H), 5.38 (bs, 1H), 5.63 (bs, 1H), 6.94–7.00 (m, 4H), 7.15–7.19 (m, 4H).

Synthesis of N-isopropyl 3,3-bis(3-fluorophenyl) propanamide (Compound 4)

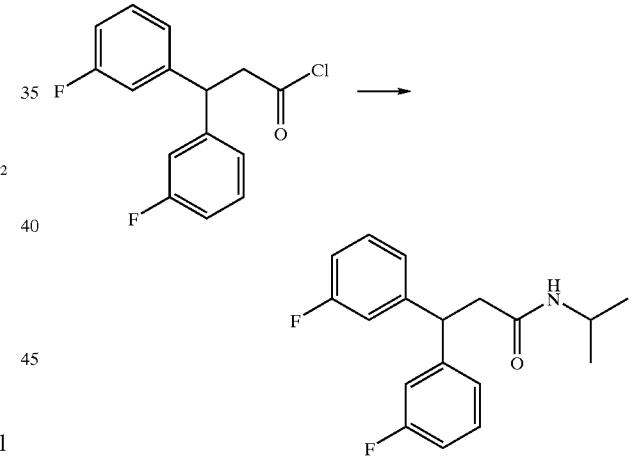

To a −78° C. solution of the acid chloride (5 g, 17.8 mmol [15.5 mmol actual]) in $CH_2Cl_2$ (50 mL) was added in a stream isopropylamine (4.6 mL, 3.16 g, 53.5 mmol, 3 equivt). The dry-ice bath was removed and the reaction mixture was then stirred for 4 h at room temperature. The mixture was then poured into diethyl ether (100 mL) and the organic layer was washed with 1 M HCl (4×50 mL), 1 M NaOH (3×50 mL), and $H_2O$ (3×50 mL). The organic layer was then filtered (paper), dried (anhydr. $Na_2SO_4$), filtered again, and the solvent was removed under vacuum to provide 3.17 g, 71% of product as a cream-colored powder. TLC analysis: Hex/EtOAc [3:1], showed one major spot. This material was recrystallized from abs. EtOH/$H_2O$ [1:1] (60 mL) plus abs. $H_2O$ (10 mL, to cloudpoint) to provide 3.06 g, 68% yield of product as a chalky, white powder. TLC: Hex/EtOAc [1:1], Rf=0.53; GC/EIMS, Rt=7.55 min, m/z 303.

Synthesis of N-[(3-hydroxy-2-methyl)-2-propyl]-3,3-bis(3-fluorophenyl)propanamide (Compound 6)

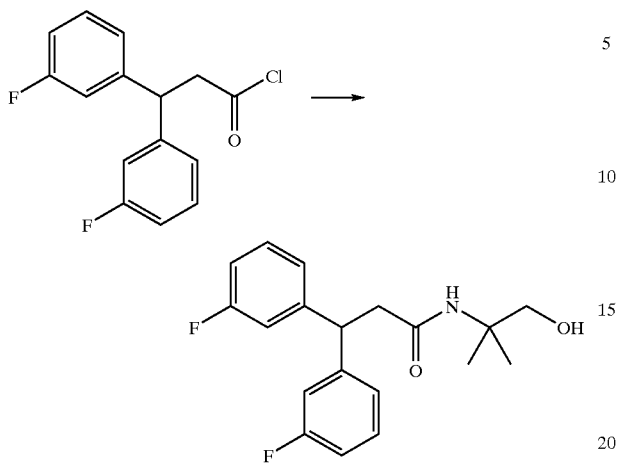

To a −78° C. solution of the acid chloride (5 g, 17.8 mmol [15.5 mmol actual]) in CH$_2$Cl$_2$ (50 mL) was added in a stream ethanolamine (5.1 mL, 4.77 g, 53.5 mmol, 3 equivt). The dry-ice bath was removed and the reaction mixture was then stirred at room temperature. The mixture was then poured into ethyl acetate (100 mL) and the organic layer was washed with 1 M HCl/sat. with NaCl (2×50 mL), 1 M NaOH/sat. with NaCl (2×50 mL), and sat. aq. NaCl (2×50 mL). The organic layer was then filtered (paper), dried (anhydr. Na$_2$SO$_4$), filtered again, and the solvent was removed under vacuum to provide ~4 g of product as an off-white powder. TLC analysis: Hex/EtOAc [3:1], showed one major spot. This material was recrystallized from abs. EtOH/H$_2$O [1:1] (50 mL) plus abs. H$_2$O (40 mL, to cloudpoint) to provide 2.70 g, 47.6% yield of product as a white powder. TLC: Hex/EtOAc [1:1], Rf=0.27; GC/EIMS Rt=6.80 min, m/z=315 (dehydration product), GC/EIMS, inconclusive mixture; $^1$H-NMR analysis indicated product present and of high purity.

Synthesis of N-methyl-2,2-bis(4-fluorophenyl)acetamide (Compound 14)

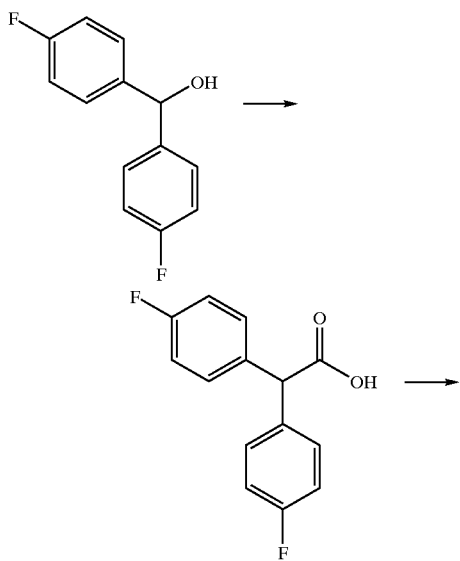

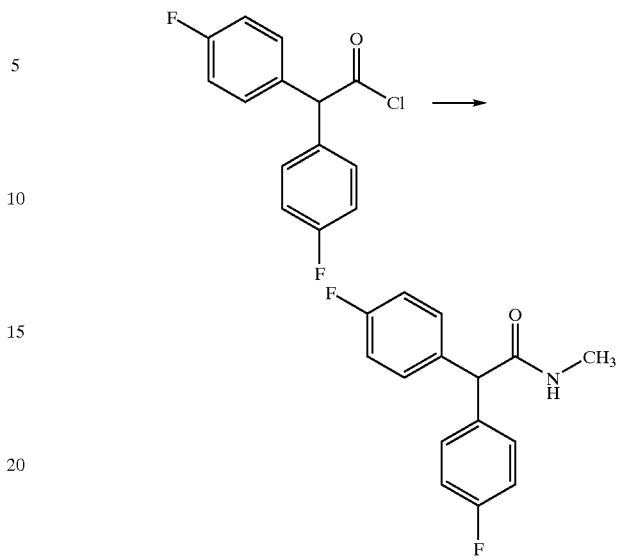

(a) Preparation of 2,2-bis(4-fluorophenyl)acetic acid

To 4,4'-difluorobenzhydrol (10.0 g, 45.4 mmol, 1 equiv) in H$_2$SO$_4$ (37 M; 200 mL, 7.4 mol, 160 equiv) in an ice bath was added formic acid (20 mL, 24 g, 0.53 mol, 12 equiv) with no stirring. After a few seconds, carbon monoxide evolution was observed. The reaction was allowed to stand without stirring for 3.5 h. The reaction mixture was carefully poured into H$_2$O (1000 mL) (highly exothermic). The aqueous mixture was extracted with EtOAc (1×250 mL). The organic layer was dried (anh. Na$_2$SO$_4$) and rotary evaporated (75° C.) to yield 11.7 g of an orange oil. This oil was dissolved in Et$_2$O (100 mL) and extracted with 2 M NaOH (1×50 mL). The aqueous layer was then acidified with 12 M HCl (8 mL) and extracted with EtOAc (1×50 mL). The organic layer was dried (anh. Na$_2$SO$_4$), rotary evaporated (75° C.), and put under high vacuum for 16 h. This provided 6.15 g (54.6%) of product as a yellow, crystalline solid.

(b) Preparation of 2,2-bis(4-fluorophenyl)acetyl chloride

The carboxylic acid (6.15 g, 24.8 mmol, 1 equiv) in thionyl chloride (12 mL, 20 g, 160 mmol, 6.6 equiv) was refluxed under N$_2$ for 2 h. The reaction solution was then rotary evaporated (95° C.). This provided 6.45 g (97.6%) of product as an orange-brown oil.

(c) Preparation of N-methyl-2,2-bis(4-fluorophenyl) acetamide

Methylamine (40% in H$_2$O; 1.5 mL, 1.4 g, 0.54 g amine, 17 mmol, 3.1 equiv) was diluted with H$_2$O (30 mL). The acid chloride (1.50 g, 5.62 mmol, 1 equiv) in EtOAc (30 mL) was added to the vigorously stirring aqueous solution over a period of 3 min. The biphasic reaction mixture was stirred vigorously for 15 min. The organic layer was separated and washed with 1 M HCl/satd. aq. NaCl (3×10 mL), 1 M NaOH/satd. aq. NaCl (2×10 mL), and satd. aq. NaCl (2×10 mL). The organic layer was then dried (anh. Na$_2$SO$_4$), rotary evaporated (75° C.), and put under high vacuum for 17 h. This provided 1.19 g (81.0%) of product as an off-white, finely crystalline solid. This solid was dissolved in EtOAc (25 mL) and filtered through a 0.45-$\mu$m filter disc. Hexanes (25 mL) were added to the filtrate. The crystallizing solution was allowed to stand for 15 min. The resulting crystals were filtered, washed with hexanes (2×25 mL), and dried under high vacuum for 22 h. This provided 547 mg (37.2%) of product as a white, finely crystalline solid.

These and other examples and compounds of the present invention can be readily prepared by skilled artisans using similar, analogous, and/or homologous synthetic methods known to those in the art.

Other embodiments are within the following claims.

What is claimed is:

1. A method for treating a patient having a neurological disease or disorder comprising administering a compound having the formula

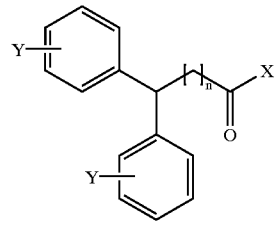

wherein:
Y is independently selected from the group consisting of —H, —F, and —Cl;
X is either —NR$^1$R$^2$ or —OR$^1$;
R$^1$ is selected from the group consisting of —H, alkyl, and hydroxyalkyl;
R$^2$ is selected from the group consisting of —H, methyl, and ethyl;
and n is either 0, 1, 2, 3, or 4.

2. The method of claim 1, wherein R$^1$ is selected from the group consisting of —H, methyl, ethyl, isopropyl, isobutyl, hydroxyisopropyl, and hydroxyethyl, and R$^2$ is —H.

3. The method of claim 1, wherein said compound has a formula selected from the group consisting of

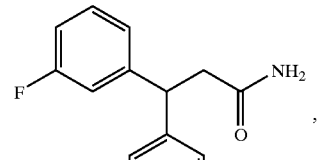

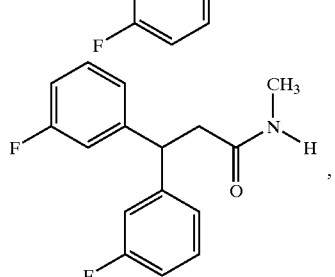

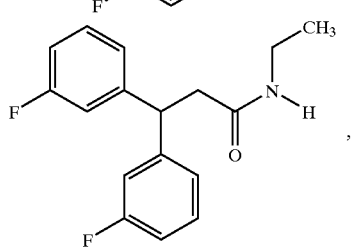

-continued

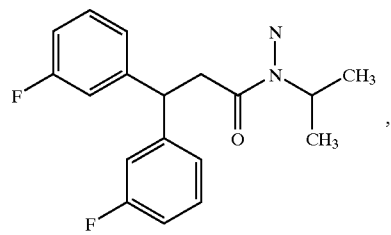

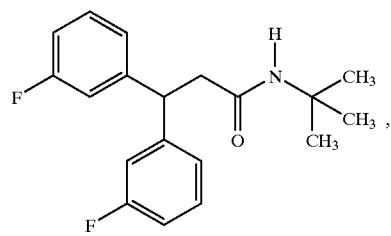

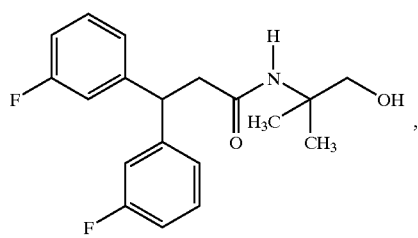

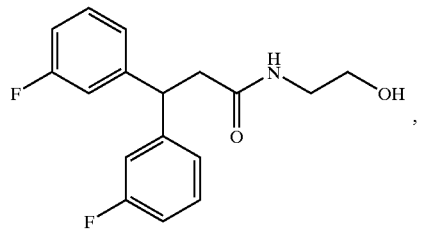

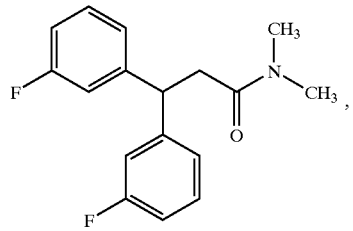

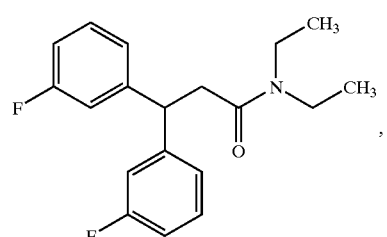

-continued
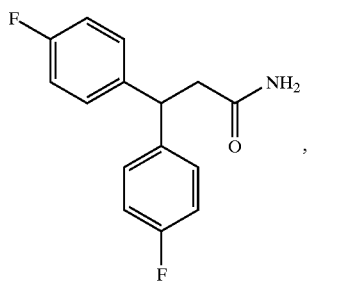
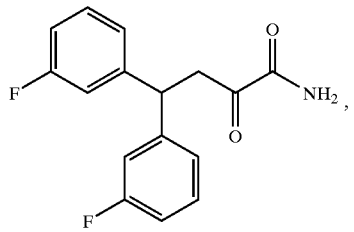
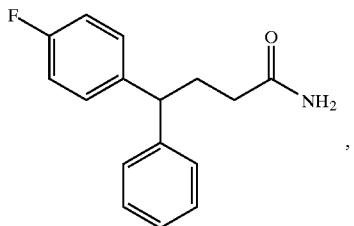
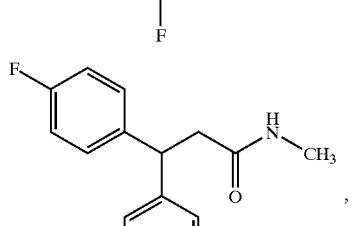
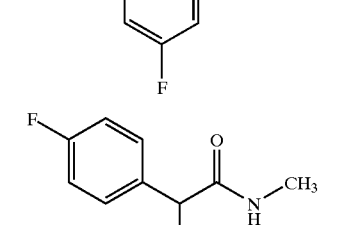
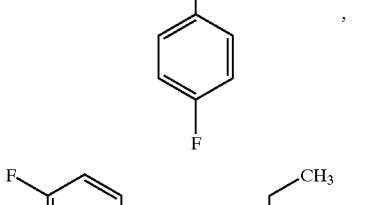
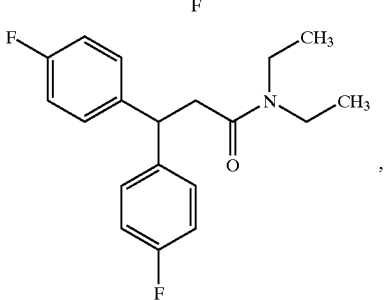
-continued
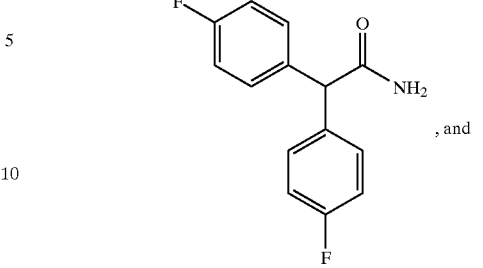, and
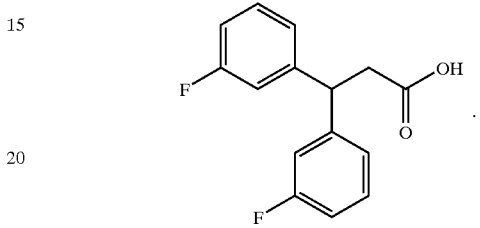
4. The method of claim 1, wherein said compound has a formula selected from the group consisting of
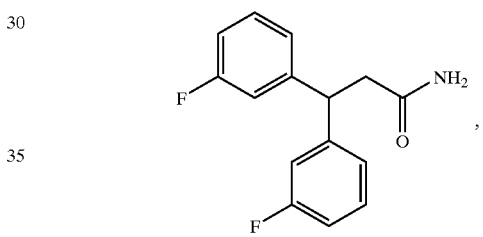
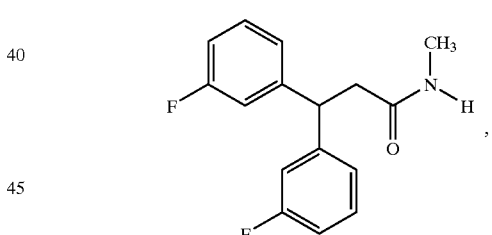
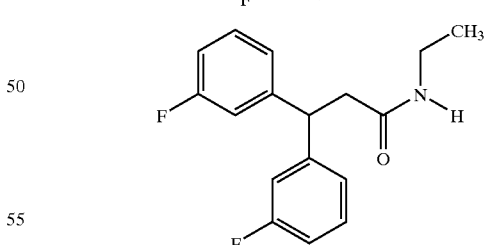
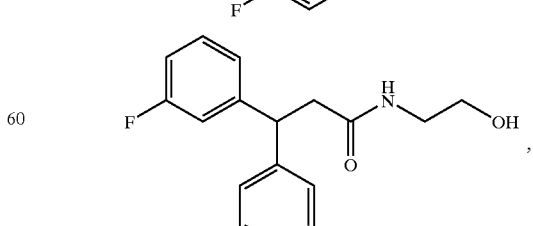

-continued
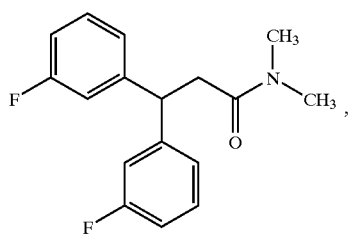
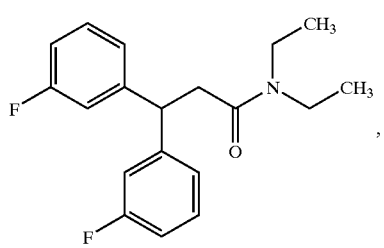
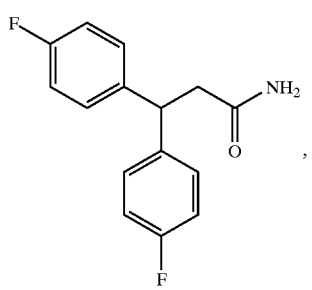
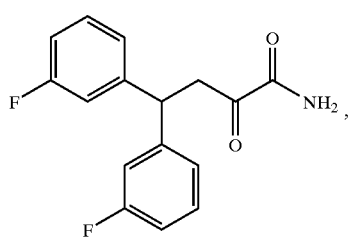
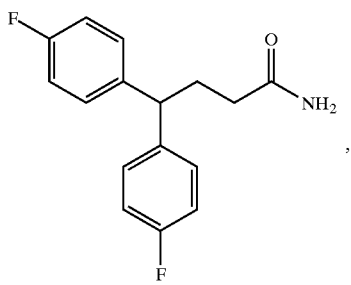
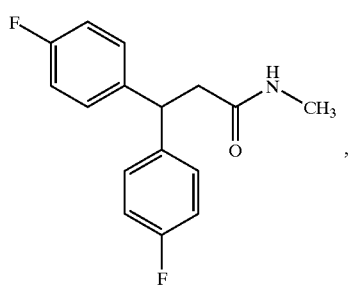
-continued
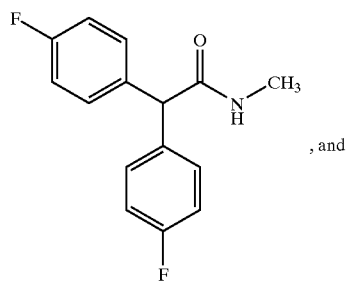, and
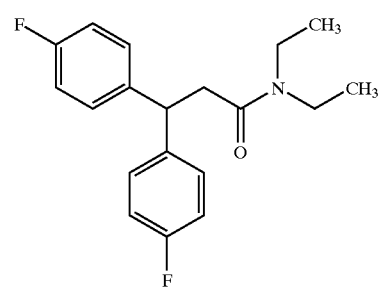
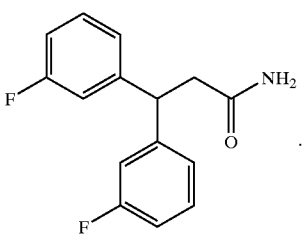
5. The method of claim 1 wherein said compound has a formula
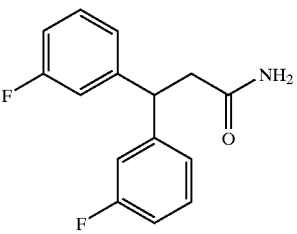.
6. A method for treating a patient having a neurological disease or disorder comprising administering to said patient a compound having the formula
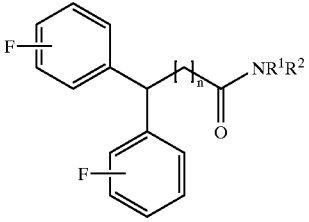

wherein:
each F is independently in either the meta- or para-position;
R[1] is selected from the group consisting of —H, alkyl, and hydroxyalkyl;
R[2] is selected from the group consisting of —H, methyl, and ethyl;
and n is 0, 1, 2, 3, or 4.

7. A method for treating a patient having a neurological disease or disorder comprising administering a compound having the formula

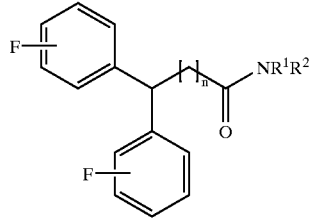

wherein:
n is 0, 1, or 2;
both F are either in the meta- or para-position;
R[1] is selected from the group consisting of —H, alkyl, and hydroxyalkyl; and
R[2] is selected from the group consisting of —H, methyl, and ethyl.

8. The method of claim 1, wherein said neurological disease or disorder is selected from the group consisting of epilepsy, convulsions, and seizure disorders.

9. The method of claim 1, wherein said treating of said patient alleviates or prevents convulsions in said patient.

10. The method of claim 1, wherein said neurological disease or disorder is associated with spasticity.

11. The method of claim 8, wherein said neurological disease or disorder is a neurodegenerative disease or disorder.

12. The method of claim 1, wherein said neurological disease or disorder is selected from the group consisting of spasticity, skeletal muscle spasms, restless leg syndrome, anxiety, stress, multiple sclerosis, stroke, head trauma, spinal cord injury, Parkinson's disease, Huntington's disease, Alzheimers disease, amyotrophic lateral sclerosis, migraine headaches, and bipolar disorder.

13. A method of alleviating or preventing a symptom of spasticity, or one or more side effects of spasticity, in a patient, comprising
administering to said patient a compound having the formula

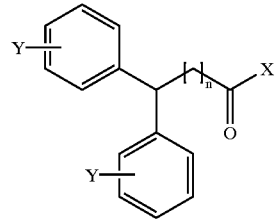

wherein:
Y is independently selected from the group consisting of —H, —F, and —Cl;
X is either —NR[1]R[2] or —OR[1];
R[1] is selected from the group consisting of —H, alkyl, and hydroxyalkyl;
R[2] is selected from the group consisting of —H, methyl, and ethyl;
and n is either 0, 1, 2, 3, or 4.

14. The method of claim 13, wherein said compound is a compound having the formula

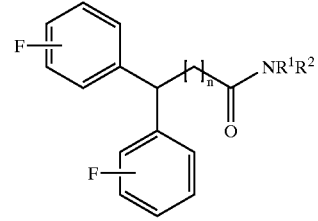

wherein:
each F is independently in either the meta- or para-position;
R[1] is selected from the group consisting of —H, alkyl, and hydroxyalkyl;
R[2] is selected from the group consisting of —H, methyl, and ethyl;
and n is either 0, 1, 2, 3, or 4.

15. The method of claim 14, wherein R[1] is selected from the group consisting of —H, methyl, ethyl, isopropyl, isobutyl, tert-butyl, hydroxyisopropyl, and hydroxyethyl, and R[2] is —H.

16. The method of claim 14, wherein n is 0, 1, or 2.

17. The method of claim 16, wherein said compound has a formula

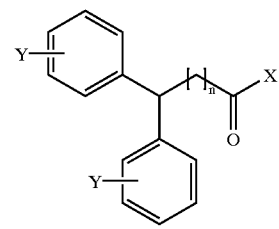

18. A method for modulating CNS activity, comprising administering to a patient a compound having the formula

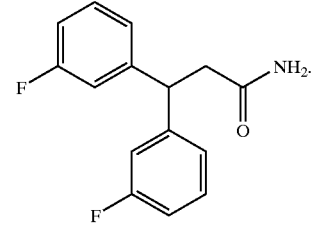

wherein:
Y is independently selected from the group consisting of —H, —F, and —Cl;
X is either —NR[1]R[2] or —OR[1];
R[1] is selected from the group consisting of —H, alkyl, and hydroxyalkyl;
R[2] is selected from the group consisting of —H, methyl, and ethyl;
and n is either 0, 1, 2, 3, or 4.

19. The method of claim 18, wherein said modulation of CNS activity alleviates a symptom associated with convulsions, spasticity, an affective mood disorder, a neuropathic pain syndrome, a headache, a restlessness syndrome, or a movement disorder.

* * * * *

UNITED STATES PATENT AND TRADEMARK OFFICE
CERTIFICATE OF CORRECTION

PATENT NO.    : 6,617,358 B1                                              Page 1 of 2
DATED         : September 9, 2003
INVENTOR(S)   : Manuel F. Balandrin et al.

It is certified that error appears in the above-identified patent and that said Letters Patent is hereby corrected as shown below:

<u>Column 28,</u>
Lines 4-13, change 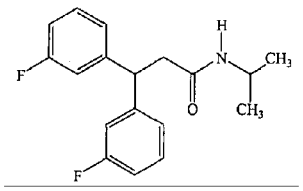 as shown in the corrected version below:

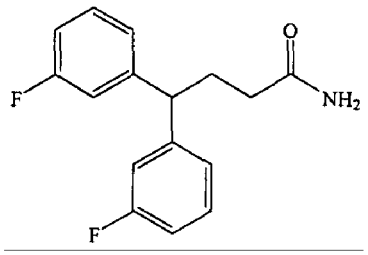

<u>Column 29,</u>
Lines 16-24, delete "O" as shown in the corrected version below:

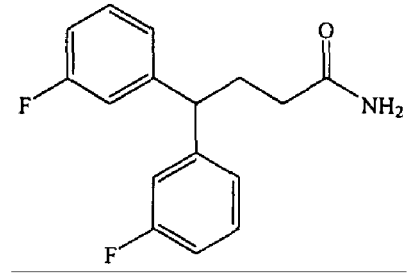

<u>Column 31,</u>
Lines 36-44, delete "O" as shown in the corrected version below:

UNITED STATES PATENT AND TRADEMARK OFFICE
CERTIFICATE OF CORRECTION

PATENT NO. : 6,617,358 B1
DATED : September 9, 2003
INVENTOR(S) : Manuel F. Balandrin et al.

It is certified that error appears in the above-identified patent and that said Letters Patent is hereby corrected as shown below:

Column 32,
Lines 28-37, delete entire structure.

Signed and Sealed this

Twenty-fourth Day of August, 2004

JON W. DUDAS
*Director of the United States Patent and Trademark Office*